US008859601B2

(12) United States Patent
Brüggemeier et al.

(10) Patent No.: US 8,859,601 B2
(45) Date of Patent: Oct. 14, 2014

(54) SUBSTITUTED BENZYL AND PHENYLSULFONYL TRIAZOLONES, AND USE THEREOF

(75) Inventors: Ulf Brüggemeier, Leichlingen (DE); Ingo Flamme, Reichshof (DE); Chantal Fürstner, Mülheim (DE); Joerg Keldenich, Wuppertal (DE); Peter Kolkhof, Wuppertal (DE); Martina Delbeck, Essen (DE); Axel Kretschmer, Wuppertal (DE); Elisabeth Pook, Wuppertal (DE); Carsten Schmeck, Mülheim (DE); Hubert Truebel, Wuppertal (DE)

(73) Assignee: Bayer Intellectual Property GmbH, Berlin (DE)

( * ) Notice: Subject to any disclaimer, the term of this patent is extended or adjusted under 35 U.S.C. 154(b) by 92 days.

(21) Appl. No.: 13/132,897

(22) PCT Filed: Nov. 26, 2009

(86) PCT No.: PCT/EP2009/008418
§ 371 (c)(1),
(2), (4) Date: Jun. 3, 2011

(87) PCT Pub. No.: WO2010/063402
PCT Pub. Date: Jun. 10, 2010

(65) Prior Publication Data
US 2011/0245308 A1    Oct. 6, 2011

(30) Foreign Application Priority Data
Dec. 6, 2008   (DE) .................. 10 2008 060 967

(51) Int. Cl.
*A61K 31/4196*  (2006.01)
*C07D 249/12*  (2006.01)

(52) U.S. Cl.
CPC .................................. *C07D 249/12* (2013.01)
USPC ....................................... 514/384; 548/263.2

(58) Field of Classification Search
CPC ..................... A61K 31/4196; C07D 249/12
USPC ................... 514/383, 384; 548/262.2, 263.2
See application file for complete search history.

(56) References Cited

U.S. PATENT DOCUMENTS

| 5,276,049 | A  | 1/1994  | Himmelsbach et al. |
| 5,281,614 | A  | 1/1994  | Ashton et al. |
| 5,326,776 | A  | 7/1994  | Winn et al. |
| 5,468,488 | A  | 11/1995 | Wahi |
| 5,585,394 | A  | 12/1996 | Di Malta et al. |
| 5,681,841 | A  | 10/1997 | Himmelsbach et al. |
| 6,531,142 | B1 | 3/2003  | Rabe et al. |
| 6,693,102 | B2 | 2/2004  | Stasch et al. |
| 6,743,798 | B1 | 6/2004  | Straub et al. |
| 6,746,989 | B1 * | 6/2004 | Muller et al. ............ 504/261 |
| 6,762,152 | B1 * | 7/2004 | Muller et al. ............ 504/273 |
| 6,833,364 | B1 | 12/2004 | Straub et al. |
| 6,838,415 | B1 | 1/2005  | Muller et al. |
| 6,864,287 | B1 | 3/2005  | Alonso-Alija et al. |
| 6,924,251 | B1 * | 8/2005 | Schwarz et al. ........... 504/242 |
| 6,969,697 | B2 * | 11/2005 | Muller et al. ............ 504/225 |
| 7,080,644 | B2 | 7/2006  | Gumaste et al. |
| 7,173,037 | B2 | 2/2007  | Alonso-Alija et al. |
| 7,279,444 | B2 * | 10/2007 | Muller et al. ............ 504/282 |
| 7,674,825 | B2 | 3/2010  | Alonso-Alija et al. |
| 2001/0020100 | A1 | 9/2001 | Manning et al. |
| 2002/0045651 | A1 | 4/2002 | Brenner et al. |
| 2002/0172644 | A1 | 11/2002 | Haslwanter et al. |
| 2003/0161790 | A1 | 8/2003 | Wahi et al. |
| 2004/0071757 | A1 | 4/2004 | Rolf |
| 2004/0082798 | A1 | 4/2004 | Alonso-Alija et al. |
| 2004/0176446 | A1 | 9/2004 | Alonso-Alija et al. |
| 2006/0148779 | A1 | 7/2006 | Bell et al. |
| 2008/0095863 | A1 | 4/2008 | Kabra et al. |
| 2009/0312381 | A1 | 12/2009 | Meier et al. |
| 2010/0261771 | A1 | 10/2010 | Brüggemeier et al. |

FOREIGN PATENT DOCUMENTS

| CA | 2327784 A1 | 3/2008 |
| EP | 051829 | 5/1982 |
| EP | 0412594 A2 | 7/1990 |
| EP | 0533276 A1 | 3/1993 |
| WO | 9931099 A1 | 6/1999 |
| WO | 0100595 A1 | 1/2001 |
| WO | 0119355 | 3/2001 |
| WO | 02066447 | 8/2002 |
| WO | 2005006892 | 1/2005 |
| WO | 2005086836 | 9/2005 |
| WO | 2005097112 A2 | 10/2005 |
| WO | 2005105779 | 11/2005 |
| WO | 2006066133 A2 | 6/2006 |
| WO | 2006117657 A1 | 11/2006 |

OTHER PUBLICATIONS

Patani et al., Chem Rev, 1996, vol. 96 (8), especially p. 3149.*
Kossentini, 2002, Physical & Chemical News, vol. 5, No. 1, p. 115-120.*
Schrier et al.,: Hormones and Hemodynamics in Heart Failure, New Engl. J. Med. 1999, vol. 341, 577-585.
DeLuca et al.,: Hyponatremia in Patients with Heart Failure, Am. J. Cardiol. 2005, vol. 96 (suppl.), 19L-23L.
Francis et al.,: Comparison of Neuroendocrine Activation in Pateients with Left Ventricular Dysfunction with and without Congestive Heart Failure, Circulation 1990, vol. 82, 1724-1729.
Saghi et al.,: Vasopressin Antagonism: a future treatment option in heart failure, Europ. Heart J. 2005, vol. 26, 538-543.

(Continued)

*Primary Examiner* — Rebecca Anderson
*Assistant Examiner* — Karen Cheng
(74) *Attorney, Agent, or Firm* — Karen B. King

(57) ABSTRACT

The present application relates to new, substituted benzyl-1,2,4-triazolones and phenylsulfonyl-1,2,4-triazolones, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

7 Claims, No Drawings

(56) References Cited

OTHER PUBLICATIONS

Palm et al., Vasopressin Antagonists as Aquaretic Agents for the Treatment of Hyponatremia, Am. J. Med. (2006) vol. 119 (7A) S87-S92.

Lemmens-Gruber, et al.: Vasopressin antagonists, Cell. Mol. Life Sci. 63 (2006) 1766-1779.

Tang et al.,: Vasopressin receptor antagonists in the management of acute heart failure, Expert Opin. Investig. Drugs, 2005, 14:5, pp. 593-600.

J. J. Bronson et al., "Discovery of the first Antibacterial Small Molecule Inhibitors of MurB," Bioorganic & Medicinal Chemistry Letters 13, 2003, pp. 873-875.

U.S. Appl. No. 12/301,616, filed Jun. 15, 2009.

U.S. Appl. No. 12/727,044, filed Feb. 16, 2011.

English translation of WO 2001/00595, filed as U.S. Appl. No. 10/019,247 on Dec. 18, 2001.

Hassan et al., "Aryl-Aryl Bond Formation One Century after the Discovery of the Ulmann Reaction," Chem Rev 2002, 102:1359-1469.

Arnswald, et al., "Unconventional Regiospecific Synthesis of Aromatic Carbonamides and Thiocarbonamides by Means of Tin-Mediated Friedel-Crafts Reactions." J. Org. Chem., 1993 58(25): 7022-7028.

Papadopoulos et al.,"Friedel-Crafts Thioacylation with Ethoxycarbonyl Isothiocyanate: A One-Step Synthesis of Aromatic Thioamides," J. Org. Chem 1976, 41(6): 962-965.

U.S. Appl. No. 13/255,515, filed Aug. 9, 2011.

U.S. Appl. No. 13/818,337, filed Feb. 22, 2013.

U.S. Appl. No. 13/819,885, filed Feb. 28, 2013.

U.S. Appl. No. 13/426,444, filed Mar. 21, 2012.

Schrier, Robert W., The sea within us: Disorders of body water homeostasis, Current Opinion in Investigational Drugs, 2007, 8(4):304-311.

Finley, et al., "Arginine Vasopressin Antagonists for the Treatment of Heart Failure and Hyponatremia," Circulation 2008, 118:410-421, p. 412, col. 2.

Sanghi, et al. "Vasopressin antagonism: a future treatment option in heart failure," European Heart Journal, 2005, 26:538-543.

Goldsmith, et al., "Current treatments and novel pharmacologic treatments for hyponatremia in congestive heart failure," Am. J. Cardiol, 2005, 95(suppl): 14B-23B.

Gines , P. et al., "Effects of stavaptan, a selective vasopressin V2 receptor antagonist, on ascites and serum sodium cirrhosis with hyponatremia," Hepatology, 2008, 48(1):204-212.

Chang et al., Triazolinones as Nonpeptide Angiotensin II Antagonists. 1. Synthesis and Evaluation of Potent 2, 4, 5-Trisubstituted Triazoloinones, J. Med. Chem. 1993, vol. 36, Nr. 17, 2558-2568.

Dobosz et al., "Synthesis and Some Pharmacological Properties of 3-(4-phenyl-5-oxo-1,2,4-triazolin-1-ylmethyl)-1,2,-triazolin-5-thione Derivatives," Acta Polomiae Pharmaceutica 2002, vol. 59, No. 4, 281-290.

Verbalis, J.G., "AVP receptor antagonists as aquaretics: Review and assessment of clinical data," Cleveland Clinic Journal of Medicine, Sep. 2009, 73, S24-S33.

* cited by examiner

SUBSTITUTED BENZYL AND PHENYLSULFONYL TRIAZOLONES, AND USE THEREOF

The present application is the National Stage of International Patent Application Number PCT/EP2009/008418, filed Nov. 26, 2009, which claims the benefit of priority of German Patent Application Number DE 102008060967.6, filed Dec. 6, 2008.

The present application relates to new, substituted benzyl-1,2,4-triazolones and phenylsulfonyl-1,2,4-triazolones, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

The liquid content of the human body is subject to various physiological control mechanisms the purpose whereof is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centres in the brain regulate drinking behaviour and control fluid excretion via the kidneys by means of humoral and neural signals. The peptide hormone vasopressin is of central importance in this [Schrier R. W., Abraham, W. T., *New Engl. J. Med.* 341, 577-585 (1999)].

Vasopressin is produced in specialized endocrine neurones in the *Nucleus supraopticus* and *N. paraventricularis* in the wall of the third ventricle (hypothalamus) and transported from there along its neural processes into the posterior lobes of the hypophysis (neurohypophysis). There the hormone is released into the bloodstream according to stimulus. A loss of volume, e.g. as a result of acute bleeding, heavy sweating, prolonged thirst or diarrhoea, is a stimulus for intensified outpouring of the hormone. Conversely, the secretion of vasopressin is inhibited by an increase in the intravascular volume, e.g. as result of increased fluid intake.

Vasopressin exerts its action mainly via binding to three receptors, which are classified as V1a, V1b and V2 receptors and belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this clinical picture excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Logically, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that by means of V2 antagonist drugs, volume homeostasis can be restored, without in the process affecting electrolyte homeostasis. Hence drugs with V2 antagonist activity appear particularly suitable for the treatment of all disease conditions which are associated with an overloading of the body with water, without the electrolytes being effectively increased in parallel. A significant electrolyte abnormality is measurable in clinical chemistry as hyponatraemia (sodium concentration <135 mmol/L); it is the most important electrolyte abnormality in hospital patients, with an incidence of ca. 5% or 250 000 cases per year in the USA alone. If the plasma sodium concentration falls below 115 mmol/L, comatose states and death are imminent.

Depending on the underlying cause, a distinction is made between hypovolaemic, euvolaemic and hypervolaemic hyponatraemia. The forms of hypervolaemia with oedema formation are clinically significant. Typical examples of this are syndrome of inappropriate ADH/vasopressin secretion (SIAD) (e.g. after craniocerebral trauma or as paraneoplasia in carcinomas) and hypervolaemic hyponatraemia in liver cirrhosis, various renal diseases and cardiac insufficiency [De Luca L. et al., *Am. J. Cardiol.* 96 (suppl.), 19L-23L (2005)]. In particular, patients with cardiac insufficiency, in spite of their relative hyponatraemia and hypervolaemia, often display elevated vasopressin levels, which is seen as the consequence of generally disturbed neurohumoral regulation in cardiac insufficiency [Francis G. S. et al., *Circulation* 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta receptor blockers on the one hand and by ACE inhibitors or angiotensin receptor blockers on the other is now an inherent part of the pharmacological treatment of cardiac insufficiency, the inappropriate elevation of vasopressin secretion in advanced cardiac insufficiency is at present still not adequately treatable. Apart from the retention of water mediated by V2 receptors and the unfavourable haemodynamic consequences associated therewith in terms of increased backload, the emptying of the left ventricle, the pressure in the pulmonary blood vessels and cardiac output are also adversely affected by V1a-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, substances which inhibit the action of vasopressin on the V2 and/or on the V1a receptor appear suitable for the treatment of cardiac insufficiency. In particular, compounds with combined activity on both vasopressin receptors (V1a and V2) should both have desirable renal and also haemodynamic effects and thus offer an especially ideal profile for the treatment of patients with cardiac insufficiency. The provision of such combined vasopressin antagonists also appears to make sense inasmuch as a volume diminution mediated solely via V2 receptor blockade can entail the stimulation of osmoreceptors and as a result a further compensatory increase in vasopressin release. As a result, in the absence of a component simultaneously blocking the V1a receptor, the harmful effects of the vasopressin, such as for example vasoconstriction and heart muscle hypertrophy, could be further intensified [Saghi P. et al., *Europ. Heart J.* 26, 538-543 (2005)].

WO 99/31099 discloses sulfonyltriazolones and triazolonealkylcarboxylic acid derivatives as integrin antagonists for the treatment, for example, of tumoral disorders. 5-Aryl-1,2,4-triazolones as vasopressin antagonists are described in WO 2007/134862. EP 0 533 276-A1 describes inter alia alkoxy-substituted triazolones as herbicides. WO 99/54315 describes triazolones with neuroprotective activity. WO 2006/066133 claims substituted aminoimidazolinones as HDAC inhibitors for the treatment of cancers and inflammatory disorders.

It is an object of the present invention to provide new compounds which act as potent, selective V2 receptor antagonists and around dual V1a/V2 receptor antagonists and are such as suitable for the treatment and/or prevention of diseases, more particularly for the treatment and/or prevention of cardiovascular disorders.

The present invention provides compounds of the general formula (I)

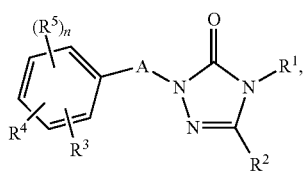

(I)

in which
A is —CH$_2$— or —SO$_2$,
R$^1$ is hydrogen, (C$_1$-C$_6$) alkyl, (C$_2$-C$_6$) alkenyl, (C$_2$-C$_6$) alkynyl or (C$_3$-C$_7$) cycloalkyl,
  where (C$_1$-C$_6$) alkyl, (C$_2$-C$_6$) alkenyl and (C$_2$-C$_6$) alkynyl may be substituted by 1 to 3 substituents independently of one another selected from the group consisting of halogen, cyano, oxo, trifluoromethyl, (C$_3$-C$_7$) cycloalkyl, phenyl, —OR$^{10}$, —NR$^{11}$R$^{12}$, —C(=O)—OR$^{13}$ and —C(=O)—NR$^{14}$R$^{15}$,
    in which (C$_3$-C$_7$) cycloalkyl may be substituted by 1 or 2 substituents independently of one another selected from the group consisting of (C$_1$-C$_4$) alkyl, oxo, hydroxyl, (C$_1$-C$_4$) alkoxy and amino,
    and
    in which phenyl may be substituted by 1 to 3 substituents independently of one another selected from the group consisting of halogen, cyano, nitro, (C$_1$-C$_4$) alkyl, trifluoromethyl, hydroxyl, hydroxymethyl, (C$_1$-C$_4$) alkoxy, trifluoromethoxy, (C$_1$-C$_4$) alkoxymethyl, hydroxycarbonyl, (C$_1$-C$_4$) alkoxycarbonyl, aminocarbonyl, mono-(C$_1$-C$_4$) alkylaminocarbonyl and di-(C$_1$-C$_4$) alkylaminocarbonyl,
    and
    in which R$^{10}$, R$^{11}$, R$^{12}$, R$^{13}$, R$^{14}$ and R$^{15}$ are each independently of one another hydrogen or (C$_1$-C$_6$) alkyl,
    in which (C$_1$-C$_6$) alkyl may be substituted on its part by 1 or 2 substituents independently of one another selected from the group consisting of amino, hydroxyl, (C$_1$-C$_4$) alkoxy, hydroxycarbonyl and (C$_1$-C$_4$) alkoxycarbonyl,
    and
  where (C$_3$-C$_7$) cycloalkyl may be substituted by 1 or 2 substituents independently of one another selected from the group consisting of (C$_1$-C$_4$) alkyl, (C$_1$-C$_4$) alkoxy, hydroxy, amino and oxo, R$^2$ is halogen, trifluoromethyl, (C$_1$-C$_6$) alkyl, (C$_1$-C$_6$) alkoxy, mono-(C$_1$-C$_6$)-alkylamino, di-(C$_1$-C$_6$)-alkylamino, (C$_3$-C$_7$) cycloalkyl, phenyl, thienyl or furyl,
  where phenyl, thienyl and furyl may be substituted by 1 to 3 substituents independently of one another selected from the group consisting of halogen, cyano, nitro, (C$_1$-C$_4$) alkyl, trifluoromethyl, hydroxyl, (C$_1$-C$_4$) alkoxy and trifluoromethoxy,
R$^3$ is hydrogen or (C$_1$-C$_4$) alkoxy,
R$_4$ is (C$_1$-C$_6$) alkylcarbonyl, hydroxycarbonyl, (C$_1$-C$_6$) alkoxycarbonyl, mono-(C$_1$-C$_6$)-alkylaminocarbonyl or di-(C$_1$-C$_6$) alkylaminocarbonyl,
  where (C$_1$-C$_6$)-alkylcarbonyl, (C$_1$-C$_6$) alkoxycarbonyl, mono-(C$_1$-C$_6$)-alkylaminocarbonyl and di-(C$_1$-C$_6$)-alkylaminocarbonyl may be substituted by 1 to 4 substituents independently of one another selected from the group consisting of halogen, trifluoromethyl, (C$_1$-C$_6$) alkyl and phenyl,
    in which phenyl may be substituted by 1 or 2 substituents independently of one another selected from the group consisting of halogen, cyano, trifluoromethyl, hydroxyl-(C$_1$-C$_4$) alkyl, (C$_1$-C$_4$) alkyl, trifluoromethoxy and (C$_1$-C$_4$) alkoxy,
R$_5$ is halogen, trifluoromethyl, (C$_1$-C$_4$) alkyl, trifluoromethoxy or (C$_1$-C$_4$) alkoxy,
n is a number 0, 1 or 2,
and also their salts, solvates, and solvates of the salts.

Compounds according to the invention are the compounds of the formula (I) and their salts, solvates, and solvates of the salts; the compounds of the below-specified formulae embraced by formula (I), and their salts, solvates, and solvates of the salts; and also the compounds specified below as working examples and embraced by formula (I), and their salts, solvates, and solvates of the salts; in so far as the below-specified compounds embraced by formula (I) are not already salts, solvates, and solvates of the salts.

Depending on their structure, the compounds according to the invention may exist in stereoisomeric forms (enantiomers, diastereomers). The present invention therefore embraces the enantiomers or diastereomers and their respective mixtures. From such mixtures of enantiomers and/or diastereomers it is possible to isolate the stereoisomerically uniform constituents in a known way.

Where the compounds according to the invention are able to occur in tautomeric forms, the present invention embraces all of the tautomeric forms.

Salts preferred in the context of the present invention are physiologically unobjectionable salts of the compounds of the invention. Also embraced are salts which, while not themselves suitable for pharmaceutical applications, may nevertheless be used, for example, for the isolation or purification of the compounds of the invention.

Physiologically unobjectionable salts of the compounds of the invention embrace acid addition salts of mineral acids, carboxylic acids and sulphonic acids, examples being salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, maleic acid, citric acid, fumaric acid, maleic acid and benzoic acid.

Physiologically unobjectionable salts of the compounds of the invention also embrace salts with customary bases, such as—by way of example and preferably—alkali metal salts (e.g. sodium and potassium salts), alkaline earth metal salts (e.g. calcium and magnesium salts) and ammonium salts, derived from ammonia or from organic amines having 1 to 16

C atoms, such as—by way of example and preferably—ethylamine, diethylamine, triethylamine, ethyldiisopropylamine, monoethanolamine, diethanolamine, trisethanolamine, dicyclohexylamine, dimethylaminoethanol, procaine, dibenzylamine, N-methylmorpholine, arginine, lysine, ethylenediamine and N-methylpiperidine.

Solvates in the context of the invention are those forms of the compounds of the invention that form a complex in solid or liquid state by coordination with solvent molecules. Hydrates are one specific form of solvates, where the coordination is with water. Preferred solvates in the context of the present invention are hydrates.

Furthermore, the present invention also embraces prodrugs of the compounds of the invention. The term "prodrugs" embraces compounds which may themselves be biologically active or inactive but which during their residence time in the body are converted (metabolically or by hydrolysis, for example) into compounds of the invention.

In the context of the present invention, the substituents, unless otherwise specified, have the following definitions:

Alkyl in the context of the invention is a linear or branched alkyl radical having 1 to 6 or 1 to 4 carbon atoms. By way of example and for preference it includes the following: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl in the context of the invention is a monocyclic saturated alkyl radical having 3 to 7 or 3 to 6 carbon atoms. By way of example and for preference it includes the following: cyclopropyl, cyclobutyl, cyclopentyl, cyclohexyl and cycloheptyl.

Alkenyl in the context of the invention is a linear or a branched alkenyl radical having 2 to 6 carbon atoms and one or two double bonds. Preference is given to a straight-chain or branched alkenyl radical having 2 to 4 carbon atoms and one double bond. By way of example and for preference it includes the following: vinyl, allyl, isopropenyl and n-but-2-en-1-yl.

Alkynyl in the context of the invention is a linear or branched alkynyl radical having 2 to 6 or 2 to 4 carbon atoms and one triple bond. By way of example and for preference it includes the following: ethynyl, n-prop-1-yn-1-yl, n-prop-2-yn-1-yl, n-but-2-yn-1-yl and n-but-3-yn-1-yl.

Alkylcarbonyl in the context of the invention is a linear or branched alkyl radical having 1 to 6 or 1 to 4 carbon atoms and a carbonyl group attached in position 1. By way of example and for preference it includes the following: methylcarbonyl, ethylcarbonyl, n-propylcarbonyl, isopropylcarbonyl, n-butylcarbonyl, isobutylcarbonyl and tert-butylcarbonyl.

Alkoxy in the context of the invention is a linear or branched alkoxy radical having 1 to 6 or 1 to 4 carbon atoms. By way of example and for preference it includes the following: methoxy, ethoxy, n-propoxy, isopropoxy, 1-methylpropoxy, n-butoxy, isobutoxy and tert-butoxy.

Alkoxycarbonyl in the context of the invention is a linear or branched alkoxy radical having 1 to 6 carbon atoms and a carbonyl group attached to the oxygen. By way of example and for preference it includes the following: methoxycarbonyl, ethoxycarbonyl, n-propoxycarbonyl, isopropoxycarbonyl and tert-butoxycarbonyl.

Mono-alkylamino in the context of the invention is an amino group having a linear or branched alkyl substituent that has 1 to 6 carbon atoms. By way of example and for preference it includes the following: methylamino, ethylamino, n-propylamino, isopropylamino, tert-butylamino, n-pentylamino and n-hexylamino.

Di-alkylamino in the context of the invention is an amino group having two identical or different linear or branched alkyl substituents each having 1 to 6 carbon atoms. By way of example and for preference it includes the following: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Mono-alkylaminocarbonyl in the context of the invention is an amino group which is linked via a carbonyl group and which has a linear or branched alkyl substituent having 1 to 6 carbon atoms.

By way of example and for preference it includes the following: methylaminocarbonyl, ethylaminocarbonyl, n-propylaminocarbonyl, isopropylaminocarbonyl, n-butylaminocarbonyl, tert-butylaminocarbonyl, n-pentylaminocarbonyl and n-hexylaminocarbonyl.

Di-alkylaminocarbonyl in the context of the invention is an amino group which is linked via a carbonyl group and which has two identical or different linear or branched alkyl substituents each having 1 to 6 or 1 to 4 carbon atoms. Preference is given to a dialkylaminocarbonyl radical having 1 to 4 carbon atoms on each alkyl group. By way of example and for preference it includes the following: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl, N-tert-butyl-N-methylaminocarbonyl, N-n-pentyl-N-methylaminocarbonyl and N-n-hexyl-N-methylaminocarbonyl.

Halogen in the context of the invention includes fluorine, chlorine, bromine and iodine. Preference is given to chlorine or fluorine.

An oxo group in the context of the invention is an oxygen atom attached via a double bond to a carbon atom.

If radicals in the compounds of the invention are substituted, the radicals, unless otherwise specified, may be substituted one or more times. In the context of the present invention it is the case that, for all radicals which occur more than once, their definitions are independent of one another. Substitution by one, two or three identical or different substituents is preferred. Very particular preference is given to substitution by one substituent.

Preference in the context of the present invention is also given to compounds of the general formula (I-A)

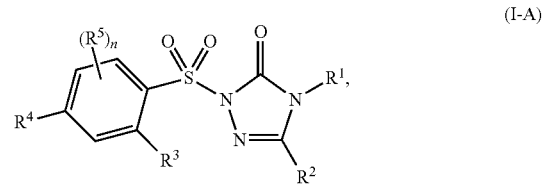

(I-A)

in which
R$^1$ is hydrogen, (C$_1$-C$_6$) alkyl, (C$_2$-C$_6$) alkenyl, (C$_2$-C$_6$) alkynyl or (C$_3$-C$_7$) cycloalkyl,
where (C$_1$-C$_6$) alkyl, (C$_2$-C$_6$) alkenyl and (C$_2$-C$_6$) alkynyl may be substituted by 1 to 3 substituents independently of one another selected from the group consisting of halogen, cyano, oxo, trifluoromethyl, (C$_3$-C$_7$) cycloalkyl, phenyl, —OR$^{10}$, —NR$^{11}$R$^{12}$, —C(=O)—OR$^{13}$ and —C(=O)—NR$^{14}$R$^{15}$, in which $(C_3-C_7)$ cycloalkyl may be substituted by 1 or 2 substituents independently of one another selected from the group consisting of $(C_1-C_4)$ alkyl, oxo, hydroxyl, $(C_1-C_4)$ alkoxy and amino,
and
in which phenyl may be substituted by 1 to 3 substituents independently of one another selected from the group consisting of halogen, cyano, nitro, $(C_1-C_4)$ alkyl, trifluoromethyl, hydroxyl, hydroxymethyl, $(C_1-C_4)$ alkoxy, trifluoromethoxy, $(C_1-C_4)$ alkoxymethyl, hydroxycarbonyl, $(C_1-C_4)$ alkoxycarbonyl, aminocarbonyl, mono-$(C_1-C_4)$-alkylaminocarbonyl and di-$(C_1-C_4)$-alkylaminocarbonyl,
and
in which $R^{10}$, $R^{11}$, $R^{12}$, $R^{13}$, $R^{14}$ and $R^{15}$ independently of one another are each hydrogen or $(C_1-C_6)$ alkyl,
in which $(C_1-C_6)$ alkyl in turn may be substituted by 1 or 2 substituents independently of one another selected from the group consisting of amino, hydroxyl, $(C_1-C_4)$ alkoxy, hydroxycarbonyl and $(C_1-C_4)$ alkoxycarbonyl
and
where $(C_3-C_7)$ cycloalkyl may be substituted by 1 or 2 substituents independently of one another selected from the group consisting of $(C_1-C_4)$ alkyl, $(C_1-C_4)$ alkoxy, hydroxyl, amino and oxo,
$R^2$ is halogen, trifluoromethyl, $(C_1-C_6)$ alkyl, $(C_1-C_6)$ alkoxy, mono-$(C_1-C_6)$-alkylamino, di-$(C_1-C_6)$-alkylamino, $(C_3-C_7)$ cycloalkyl, phenyl, thienyl or furyl,
where phenyl, thienyl and furyl may be substituted by 1 to 3 substituents independently of one another selected from the group consisting of halogen, cyano, nitro, $(C_1-C_4)$ alkyl, trifluoromethyl, hydroxyl, $(C_1-C_4)$ alkoxy and trifluoromethoxy,
$R^3$ is hydrogen or $(C_1-C_4)$ alkoxy,
$R^4$ is $(C_1-C_6)$ alkylcarbonyl, $(C_1-C_6)$ alkoxycarbonyl, mono-$(C_1-C_6)$-alkylaminocarbonyl or di-$(C_1-C_6)$-alkylaminocarbonyl,
where $(C_1-C_6)$ alkylcarbonyl, $(C_1-C_6)$ alkoxycarbonyl, mono-$(C_1-C_6)$-alkylaminocarbonyl and di-$(C_1-C_6)$-alkylaminocarbonyl may be substituted by 1 to 4 substituents independently of one another selected from the group consisting of halogen, $(C_1-C_6)$ alkyl and phenyl,
in which phenyl may be substituted by 1 or 2 substituents independently of one another selected from the group consisting of halogen, cyano, trifluoromethyl, hydroxyl-$(C_1-C_4)$ alkyl, $(C_1-C_4)$ alkyl, trifluoromethoxy and $(C_1-C_4)$ alkoxy,
$R^5$ is halogen, trifluoromethyl, $(C_1-C_4)$ alkyl, trifluoromethoxy or $(C_1-C_4)$ alkoxy,
n is a number 0, 1 or 2,
and also their salts, solvates, and solvates of the salts.

Preference in the context of the present invention is given to compounds of the formula (I), in which
A is —$CH_2$— or —$SO_2$—,
$R^1$ is hydrogen, $(C_1-C_6)$ alkyl, $(C_2-C_4)$ alkenyl or $(C_3-C_6)$ cycloalkyl,
where $(C_1-C_6)$ alkyl and $(C_2-C_4)$ alkenyl may be substituted by 1 to 3 substituents independently of one another selected from the group consisting of fluorine, chlorine, oxo, trifluoromethyl, $(C_3-C_6)$ cycloalkyl, phenyl, —$OR^{10}$, —$NR^{11}R^{12}$, —C(=O)—$OR^{13}$ and —C(=O)—$NR^{14}R^{15}$,
in which phenyl may be substituted by 1 to 3 substituents independently of one another selected from the group consisting of fluorine, chlorine, $(C_1-C_4)$ alkyl, trifluoromethyl, hydroxyl, $(C_1-C_4)$ alkoxy, trifluoromethoxy, hydroxycarbonyl, $(C_1-C_4)$ alkoxycarbonyl, aminocarbonyl, mono-$(C_1-C_4)$-alkylaminocarbonyl and di-$(C_1-C_4)$-alkylaminocarbonyl,
and
in which $R^{10}$, $R^{11}$, $R^{12}$, $R^{13}$, $R^{14}$ and $R^{15}$ independently of one another are each hydrogen or $(C_1-C_6)$ alkyl,
$R^2$ is chlorine, bromine, trifluoromethyl, $(C_1-C_4)$ alkyl, $(C_1-C_4)$ alkoxy, mono-$(C_1-C_4)$-alkylamino, di-$(C_1-C_4)$-alkylamino, $(C_3-C_6)$ cycloalkyl or phenyl,
where phenyl may be substituted by 1 to 3 substituents independently of one another selected from the group consisting of fluorine, chlorine, cyano, methyl, ethyl, trifluoromethyl, hydroxyl, methoxy, ethoxy and trifluoromethoxy,
$R^3$ is hydrogen or methoxy,
$R^4$ is $(C_1-C_6)$ alkylcarbonyl, hydroxycarbonyl, $(C_1-C_6)$ alkoxycarbonyl, mono-$(C_1-C_6)$-alkylaminocarbonyl or di-$(C_1-C_6)$-alkylaminocarbonyl,
where mono-$(C_1-C_6)$-alkylaminocarbonyl and di-$(C_1-C_6)$-alkylaminocarbonyl may be substituted by 1 to 4 substituents independently of one another selected from the group consisting of fluorine, trifluoromethyl, $(C_1-C_4)$ alkyl and phenyl,
in which phenyl may be substituted by 1 or 2 substituents independently of one another selected from the group consisting of fluorine, chlorine, trifluormethyl, methyl, ethyl, trifluoromethoxy, methoxy and ethoxy,
$R^5$ is fluorine, chlorine, trifluoromethyl, methyl, ethyl, trifluoromethoxy, methoxy or ethoxy,
n is a number 0 or 1,
and also their salts, solvates, and solvates of the salts.

Preference in the context of the present invention is also given to compounds of the formula (I-A) in which
$R^1$ is hydrogen, $(C_1-C_6)$ alkyl, $(C_2-C_4)$ alkenyl or $(C_3-C_6)$ cycloalkyl,
where $(C_1-C_6)$ alkyl and $(C_2-C_4)$ alkenyl may be substituted by 1 to 3 substituents independently of one another selected from the group consisting of fluorine, chlorine, oxo, trifluoromethyl, $(C_3-C_6)$ cycloalkyl, phenyl, —$OR^{10}$, —$NR^{11}R^{12}$, —C(=O)—$OR^{13}$ and —C(=O)—$NR^{14}R^{15}$,
in which phenyl may be substituted by 1 to 3 substituents independently of one another selected from the group consisting of fluorine, chlorine, $(C_1-C_4)$ alkyl, trifluoromethyl, hydroxyl, $(C_1-C_4)$ alkoxy, trifluoromethoxy, hydroxycarbonyl, $(C_1-C_4)$ alkoxycarbonyl, aminocarbonyl, mono-$(C_1-C_4)$-alkylaminocarbonyl and di-$(C_1-C_4)$-alkylaminocarbonyl,
and
in which $R^{10}$, $R^{11}$, $R^{12}$, $R^{13}$, $R^{14}$ and $R^{15}$ independently of one another are each hydrogen or $(C_1-C_6)$ alkyl,
$R^2$ is chlorine, bromine, trifluoromethyl, $(C_1-C_4)$ alkyl, $(C_1-C_4)$ alkoxy, mono-$(C_1-C_4)$-alkylamino, di-$(C_1-C_4)$-alkylamino, $(C_3-C_6)$ cycloalkyl or phenyl,
where phenyl may be substituted by 1 to 3 substituents independently of one another selected from the group consisting of halogen, cyano, nitro, $(C_1-C_4)$ alkyl, trifluoromethyl, hydroxyl, $(C_1-C_4)$ alkoxy and trifluoromethoxy,
$R^3$ is hydrogen or $(C_1-C_4)$ alkoxy,
$R^4$ is $(C_1-C_6)$ alkylcarbonyl, $(C_1-C_6)$ alkoxycarbonyl, mono-$(C_1-C_6)$-alkylaminocarbonyl or di-$(C_1-C_6)$-alkylaminocarbonyl,
where mono-$(C_1-C_6)$-alkylaminocarbonyl and di-$(C_1-C_6)$-alkylaminocarbonyl may be substituted by 1 to 4 substituents independently of one another selected from the group consisting of $(C_1$-$C_6)$ alkyl and phenyl,
in which phenyl may be substituted by 1 or 2 substituents independently of one another selected from the group consisting of fluorine, chlorine, trifluoromethyl, $(C_1$-$C_4)$ alkyl, trifluoromethoxy and $(C_1$-$C_4)$ alkoxy, $R^5$ is fluorine, chlorine, trifluoromethyl, methyl, ethyl, trifluoromethoxy, methoxy or ethoxy, n is a number 0 or 1, and also their salts, solvates, and solvates of the salts.

Particular preference in the context of the present invention is given to compounds of the formula (I) in which A is —$CH_2$— or —$SO_2$—, $R^1$ is hydrogen, $(C_1$-$C_6)$ alkyl, $(C_2$-$C_4)$ alkenyl or cyclopropyl,
where $(C_1$-$C_6)$ alkyl and $(C_2$-$C_4)$ alkenyl may be substituted by 1 to 3 substituents independently of one another selected from the group consisting of fluorine, oxo, trifluoromethyl, phenyl, —$OR^{10}$, —$NR^{11}R^{12}$, —C(=O)—$OR^{13}$ and —C(=O)—$NR^{14}R^{15}$,
in which phenyl may be substituted by 1 to 3 substituents independently of one another selected from the group consisting of fluorine, chlorine, methyl, ethyl, trifluoromethyl, hydroxyl, methoxy, ethoxy, trifluoromethoxy, hydroxycarbonyl, methoxycarbonyl and ethoxycarbonyl,
and
in which $R^{10}$, $R^{11}$, $R^{12}$, $R^{13}$, $R^{14}$ and $R^{15}$ independently of one another are each hydrogen or methyl, $R^2$ is chlorine, bromine, trifluoromethyl, $(C_1$-$C_4)$ alkyl, $(C_1$-$C_4)$ alkoxy, mono-$(C_1$-$C_4)$-alkylamino, di-$(C_1$-$C_4)$-alkylamino, cyclopropyl or phenyl,
where phenyl may be substituted by 1 or 2 substituents independently of one another selected from the group consisting of fluorine, chlorine, methyl, ethyl, trifluoromethyl, hydroxyl, methoxy, ethoxy and trifluoromethoxy, $R^3$ is hydrogen or methoxy, $R^4$ is methylcarbonyl, ethylcarbonyl, methoxycarbonyl, ethoxycarbonyl, mono-$(C_1$-$C_6)$-alkylaminocarbonyl or di-$(C_1$-$C_6)$-alkylaminocarbonyl,
where mono-$(C_1$-$C_6)$-alkylaminocarbonyl and di-$(C_1$-$C_6)$-alkylaminocarbonyl may be substituted by 1 to 4 substituents independently of one another selected from the group consisting of fluorine, trifluoromethyl, methyl, ethyl and phenyl,
in which phenyl may be substituted by 1 or 2 substituents independently of one another selected from the group consisting of fluorine, chlorine, trifluoromethyl, methyl, ethyl, trifluoromethoxy, methoxy and ethoxy, $R^5$ is fluorine, chlorine or trifluoromethyl, n is a number 0 or 1, and also their salts, solvates, and solvates of the salts.

Particular preference in the context of the present invention is given to compounds of the formula (I-A) in which $R^1$ is hydrogen, $(C_1$-$C_6)$ alkyl, $(C_2$-$C_4)$ alkenyl or cyclopropyl,
where $(C_1$-$C_6)$ alkyl and $(C_2$-$C_4)$ alkenyl may be substituted by 1 to 3 substituents independently of one another selected from the group consisting of fluorine, oxo, trifluoromethyl, phenyl, —$OR^{10}$, —$NR^{11}R^{12}$, —C(=O)—$OR^{13}$ and —C(=O)—$NR^{14}R^{15}$,
in which phenyl may be substituted by 1 to 3 substituents independently of one another selected from the group consisting of fluorine, chlorine, methyl, ethyl, trifluoromethyl, hydroxyl, methoxy, ethoxy, trifluoromethoxy, hydroxycarbonyl, methoxycarbonyl and ethoxycarbonyl,
and
in which $R^{10}$, $R^{11}$, $R^{12}$, $R^{13}$, $R^{14}$ and $R^{15}$ independently of one another are each hydrogen or $(C_1$-$C_4)$ alkyl, $R^2$ is chlorine, bromine, trifluoromethyl, $(C_1$-$C_4)$ alkyl, $(C_1$-$C_4)$ alkoxy, mono-$(C_1$-$C_4)$-alkylamino, di-$(C_1$-$C_4)$-alkylamino, cyclopropyl or phenyl,
where phenyl may be substituted by 1 or 2 substituents independently of one another selected from the group consisting of fluorine, chlorine, methyl, ethyl, trifluoromethyl, hydroxyl, methoxy, ethoxy and trifluoromethoxy, $R^3$ is hydrogen or $(C_1$-$C_4)$ alkoxy, $R^4$ is methylcarbonyl, ethylcarbonyl, methoxycarbonyl, ethoxycarbonyl, mono-$(C_1$-$C_6)$-alkylaminocarbonyl or di-$(C_1$-$C_4)$-alkylaminocarbonyl,
where mono-$(C_1$-$C_6)$-alkylaminocarbonyl and di-$(C_1$-$C_4)$-alkylaminocarbonyl may be substituted by 1 to 4 substituents independently of one another selected from the group consisting of methyl, ethyl and phenyl,
in which phenyl may be substituted by 1 or 2 substituents independently of one another selected from the group consisting of fluorine, trifluoromethyl, $(C_1$-$C_4)$ alkyl, trifluoromethoxy, methoxy and ethoxy, and also their salts, solvates, and solvates of the salts.

Preference is also given to compounds of the formula (I) in which A is —$CH_2$—.

Preference is also given to compounds of the formula (I) in which A is —$SO_2$—.

Preference is also given to compounds of the formula (I) in which $R^4$ is mono-$(C_1$-$C_6)$-alkylaminocarbonyl or di-$(C_1$-$C_6)$-alkylaminocarbonyl,
where mono-$(C_1$-$C_6)$-alkylaminocarbonyl and di-$(C_1$-$C_6)$-alkylaminocarbonyl may be substituted by 1 to 4 substituents independently of one another selected from the group consisting of fluorine, trifluoromethyl and phenyl,
in which phenyl is substituted by 1 or 2 substituents independently of one another selected from the group consisting of fluorine, chlorine, trifluoromethyl, methyl, ethyl, trifluoromethoxy, methoxy and ethoxy.

The radical definitions given individually in the respective combinations and preferred combinations of radicals are also replaced arbitrarily, independently of the particular radical combinations specified, by radical definitions from other combinations.

Very particular preference is given to combinations from two or more of the above-mentioned ranges of preference.

The invention further provides a process for preparing the compounds of the formula (I) according to the invention, characterized in that

[A] a compound of the formula (II)

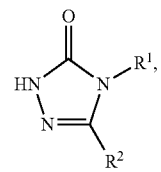

in which $R^1$ and $R^2$ are each as defined above is reacted in an inert solvent, in the presence of a suitable base, with a compound of the formula (III)

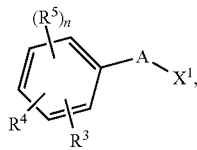
(III)

in which A, n, $R^3$, $R^4$ and $R^5$ are each as defined above, and $X^1$ is halogen, in particular chlorine, or

[B] from a compound of the formula (IV)

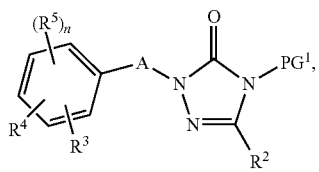
(IV)

in which A, n, $R^2$, $R^3$, $R^4$ and $R^5$ are each as defined above, and $PG^1$ is a suitable protective group, for example allyl, in an inert solvent by standard methods the protective group $PG^1$ is eliminated and the resulting compound of the formula (V)

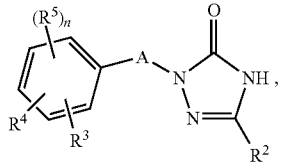
(V)

in which A, n, $R^2$, $R^3$, $R^4$ and $R^5$ are each as defined above, is reacted in the presence of a suitable base with a compound of the formula (VI)

$R^1$—$X^2$ (VI), in which $R^1$ is as defined above, and $X^2$ is a leaving group, such as, for example, halogen, mesylate or tosylate, and the resulting compounds of the formula (I) are converted optionally with the corresponding (i) solvents and/or (ii) bases or acids into their solvates, salts and/or solvates of the salts.

The preparation of the compounds of the invention may be illustrated by the following synthesis schemes:

Scheme 1

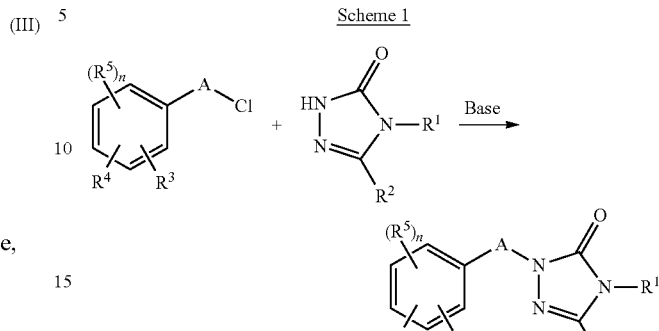

Scheme 2

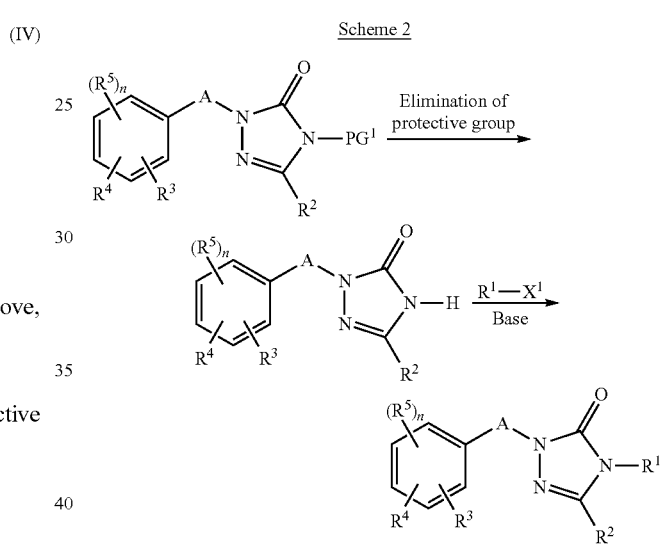

Inert solvents for the process step (II)+(III)→(I) are for example ethers such as diethyl ether, dioxan, tetrahydrofuran, glycol dimethyl ether or diethylene glycol dimethyl ether, hydrocarbons such as benzene, toluene, xylene, hexane, cyclohexane or petroleum fractions, halogenated hydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide (DMF), N,N'-dimethylpropyleneurea (DMPU) or N-methylpyrrolidone (NMP). Likewise it is possible to use mixtures of the said solvents. Acetone, tetrahydrofuran, dimethylformamide or mixtures of these solvents are preferred.

As bases for the process step (II)+(III)→(I), the usual inorganic or organic bases are suitable. These preferably include alkali metal hydroxides such as for example lithium, sodium or potassium hydroxide, alkali metal or alkaline earth metal carbonates such as lithium, sodium, potassium or caesium carbonate, alkali metal alcoholates such as sodium or potassium methanolate, sodium or potassium ethanolate or lithium, sodium or potassium tert-butylate, alkali metal hydrides such as sodium or potassium hydride, amides such as sodamide, lithium or potassium bis(trimethylsilyl)amide or lithium diisopropylamide, or organic amines such as N,N- diisopropylethylamine, 1,5-diazabicyclo[4.3.0] non-5-ene (DBN) or 1,8-diazabicyclo[5.4.0] undec-7-ene (DBU). Preferably, sodium hydride and potassium tert-butylate are used.

In this case, the base is used in an amount of 1 to 5 mol, preferably in an amount of 1 to 2.5 mol, based on 1 mol of the compound of the formula (IV). The reaction generally takes place in a temperature range from −78° C. to +50° C., preferably at −78° C. to +30° C. The reaction can take place under standard atmospheric, increased or reduced pressure (e.g. from 0.5 to 5 bar). The operation is generally carried out under atmospheric pressure.

Inert solvents for the process step (V)+(VI)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, halogenated hydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide (DMF), N,N'-dimethylpropyleneurea (DMPU) or N-methylpyrrolidone (NMP). It is also possible to use mixtures of the stated solvents. Preference is given to using dimethylformamide.

The protective group is eliminated in process step (IV)→(V) in accordance with the methods known to the skilled person [cf. e.g. B. T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. Where $PG^1$ is allyl, the elimination is accomplished preferably with formic acid in dioxane or dimethylformamide in the presence of a suitable palladium catalyst such as, for example, tetrakis(triphenylphosphine)palladium(0) and of an amine base such as, for example, triethylamine.

As bases for the process step (V)+(VI)→(I), the usual inorganic or organic bases are suitable. These preferably include alkali metal hydroxides such as for example lithium, sodium or potassium hydroxide, alkali metal or alkaline earth metal carbonates such as lithium, sodium, potassium or caesium carbonate, alkali metal alcoholates such as sodium or potassium methanolate, sodium or potassium ethanolate or lithium, sodium or potassium tert-butylate, alkali metal hydrides such as sodium or potassium hydride, amides such as sodamide, lithium or potassium bis(trimethylsilyl)amide or lithium diisopropylamide, or organic amines such as N,N-diisopropylethylamine, 1,5-diazabicyclo[4.3.0]non-5-ene (DBN) or 1,8-diazabicyclo[5.4.0]undec-7-ene (DBU). Preference is given to using caesium carbonate.

In this case, the base is used in an amount of 1 to 5 mol, preferably in an amount of 1 to 2.5 mol, based on 1 mol of the compound of the formula (IV). The reaction takes place in general in a temperature range from 0° C. to +100° C., preferably at +25° C. to +80° C. The reaction can take place under standard atmospheric, increased or reduced pressure (e.g. from 0.5 to 5 bar), optionally in a microwave. The operation is generally carried out under atmospheric pressure.

Further compounds of the invention may optionally also be prepared by conversions of functional groups of individual substituents, more particularly those set out under $R^4$, starting from the compounds of the formula (I) obtained by the processes above. These conversions are carried out in accordance with customary methods customary methods known to the skilled person, and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, especially formation of carboxamides, and also introduction and removal of temporary protective groups.

The synthesis scheme below is intended to illustrate these conversions by way of example:

Scheme 3

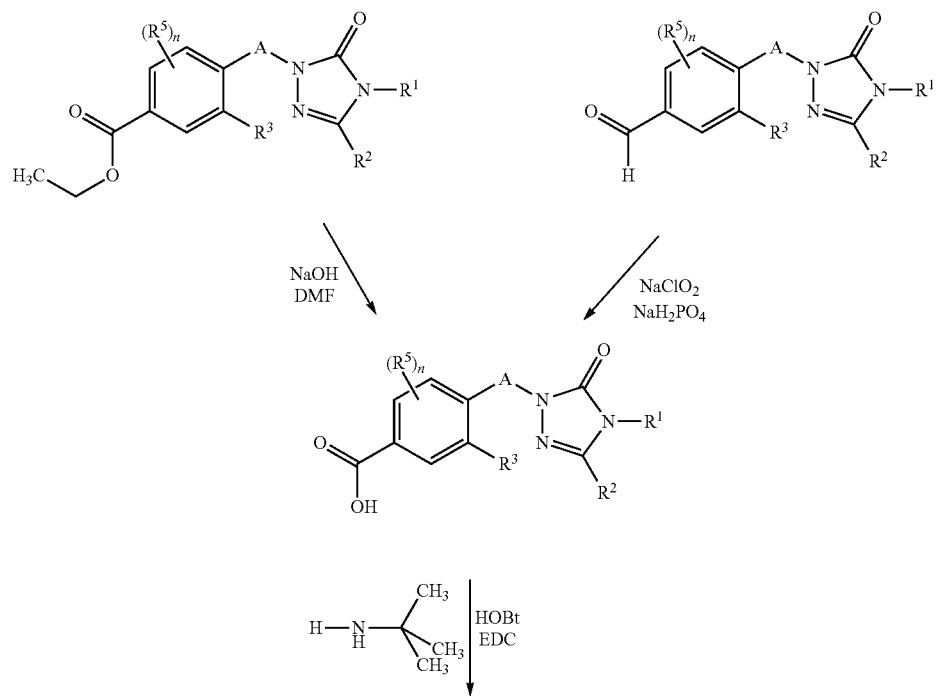

-continued

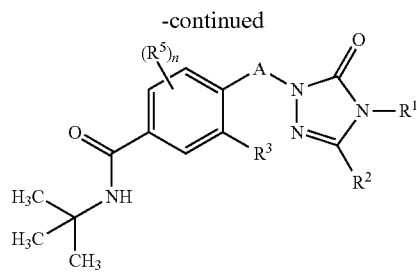

Suitable condensation agents for the amidation include, for example, carbodiimides such as N,N'-diethyl-, N,N'-dipropyl-, N,N'-diisopropyl- or N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium-3 sulphate or 2-tert-butyl-5-methyl-isoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis-(2-oxo-3-oxazolidinyl)phosphoryl chloride, benzotriazol-1-yloxy-tris(dimethylamino)phosphonium hexafluorophosphate, benzotriazol-1-yl-oxy-tris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with other additives such as 1-hydroxy-benzotriazole (HOBt) or N-hydroxysuccinimide (HOSu), and, as bases, alkali metal carbonates, e.g. sodium or potassium carbonate or hydrogen carbonate, or organic bases such as trialkyl-amines, e.g. triethylamine, N-methylmorpholine, N-methylpiperidine or N,N-diisopropylethyl-amine. Preferably EDC in combination with HOBt or TBTU in combination with N,N-diisopropylethylamine is used.

The amidation is generally performed in a temperature range from −20° C. to +60° C., preferably at 0° C. to +40° C. The reaction can take place under standard atmospheric, increased or reduced pressure (e.g. from 0.5 to 5 bar). The operation is generally carried out under atmospheric pressure.

The compounds of the formula (II) are known from the literature or can be prepared in analogy to processes known from the literature [cf. e.g. U.S. Pat. No. 3,780,052, EP 422469, EP 425948, EP 507171, EP 703224 and WO 2007/134862].

The compounds of the formulae (III) and (VI) are available commercially, are known from the literature, can be prepared in analogy to processes known from the literature, or can be prepared as shown by way of example in the synthesis scheme below (Scheme 5).

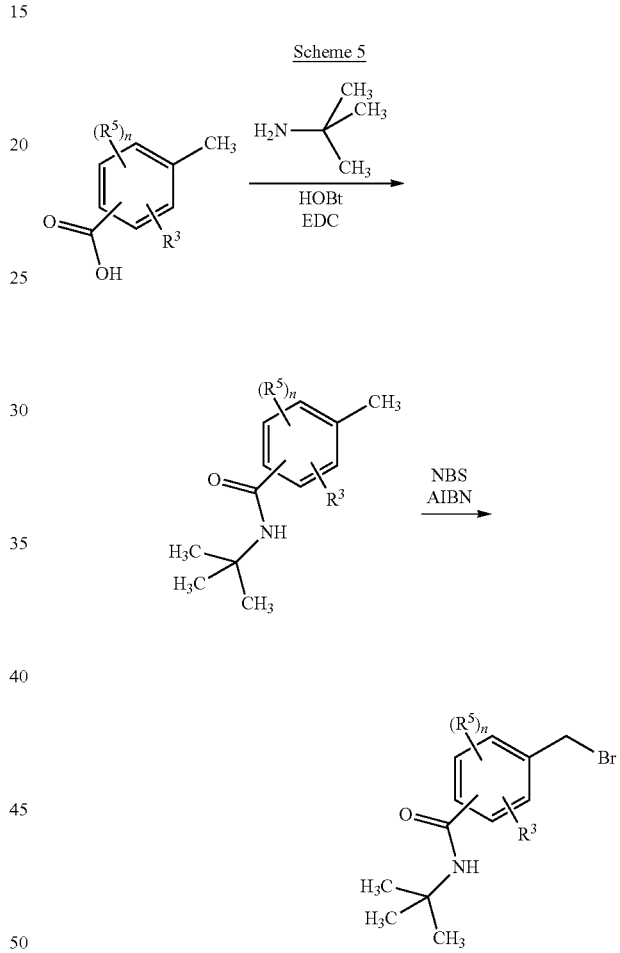

The amide coupling is carried out under reaction conditions specified above.

Suitable halogenating agents include elemental bromine with acetic acid, 1,3-dibromo-5,5-dimethylhydantoin and also, in particular, N-bromosuccinimide (NBS), N-iodosuccinimide (NIS), optionally with addition of α,α'-azobis(isobutyronitrile) (AIBN) as initiator.

Compounds of the formula (IV) can be prepared by reacting a hydrazide of the formula (VII) with an isocyanate of the formula (VIII) or with a nitrophenyl carbamate of the formula (IX) to give a compound of the formula (X), subsequently subjecting this compound (X) to base-induced cyclization to give a triazolone of the formula (XI), and reacting this triazolone with a compound (III) (Scheme 4):

Scheme 4

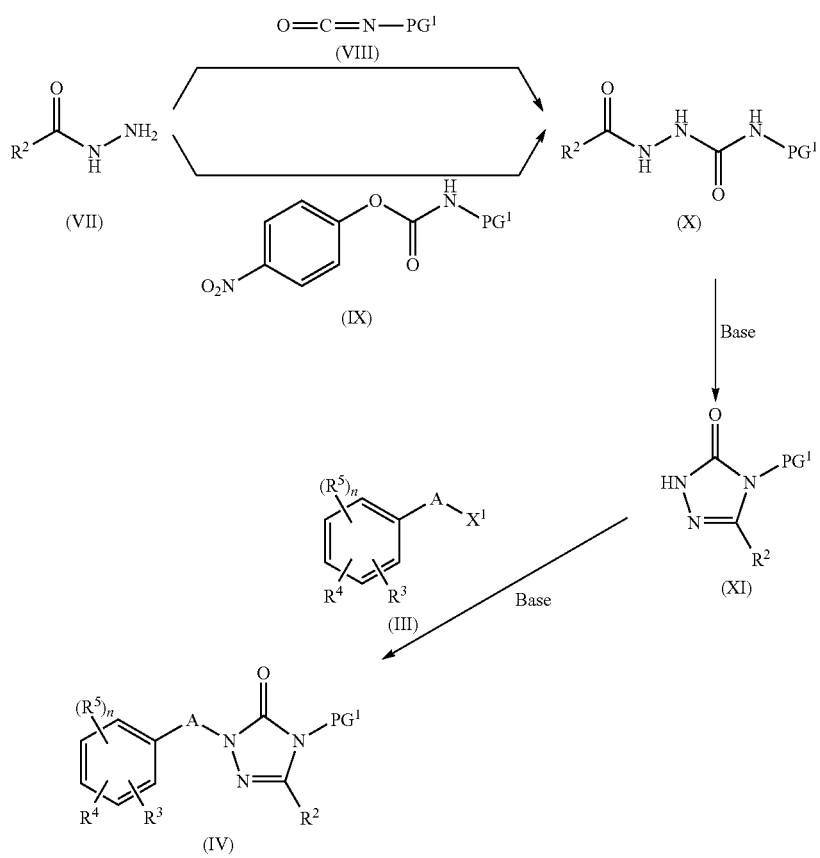

The compounds according to the invention possess valuable pharmacological properties and can be used for the prevention and/or treatment of various diseases and disease-induced states in humans and animals.

The compounds according to the invention are potent selective V2 and/or dual V1a/V2 receptor antagonists, which inhibit vasopressin activity in vitro and in vivo. Furthermore, the compounds according to the invention also act as antagonists on the related oxytozin receptor.

The compounds according to the invention are particularly suitable for the prophylaxis and/or treatment of cardiovascular diseases. In this connection, the following may for example and preferably be mentioned as target indications: acute and chronic cardiac insufficiency, arterial hypertension, coronary heart disease, stable and unstable angina pectoris, myocardial ischaemia, myocardial infarction, shock, arteriosclerosis, atrial and ventricular arrhythmias, transitory and ischaemic attacks, stroke, inflammatory cardiovascular diseases, peripheral and cardiac vascular diseases, peripheral circulation disorders, arterial pulmonary hypertension, spasms of the coronary arteries and peripheral arteries, thromboses, thromboembolic diseases, oedema formation such as for example pulmonary oedema, cerebral oedema, renal oedema or cardiac insufficiency-related oedema, and restenoses for example after thrombolysis treatments, percutaneous-transluminal angioplasties (PTA), transluminal coronary angioplasties (PTCA), heart transplants and bypass operations.

In the sense of the present invention, the term cardiac insufficiency also includes more specific or related disease forms such as right cardiac insufficiency, left cardiac insufficiency, global insufficiency, ischaemic cardiomyopathy, dilatative cardiomyopathy, congenital heart defects, heart valve defects, cardiac insufficiency with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic cardiac insufficiency, alcohol-toxic cardiomyopathy, cardiac storage diseases, diastolic cardiac insufficiency and systolic cardiac insufficiency.

Furthermore, the compounds according to the invention are suitable for use as a diuretic for the treatment of oedemas and in electrolyte disorders, in particular in hypervolaemic and euvolaemic hyponatraemia.

The compounds according to the invention are also suitable for the prophylaxis and/or treatment of polycystic kidney disease (PCKD) and syndrome of inappropriate ADH secretion (SIADH).

In addition, the compounds according to the invention can be used for the prophylaxis and/or treatment of liver cirrhosis, ascites, diabetes mellitus and diabetic complications such as for example neuropathy and nephropathy, acute and chronic kidney failure and chronic renal insufficiency.

Further, the compounds according to the invention are suitable for the prophylaxis and/or treatment of central nervous disorders such as anxiety states and depression, of glaucoma and of cancer, in particular of pulmonary tumours.

Furthermore, the compounds according to the invention can be used for the prophylaxis and/or treatment of inflammatory diseases, asthmatic diseases, chronic-obstructive respiratory tract diseases (COPD), pain conditions, prostatic hypertrophy, incontinence, bladder inflammation, hyperactive bladder, diseases of the adrenals such as for example phaeochromocytoma and adrenal apoplexy, diseases of the intestine such as for example Crohn's disease and diarrhoea, or of menstrual disorders such as for example dysmenorrhoea.

A further object of the present invention is the use of the compounds according to the invention for the treatment and/or prophylaxis of diseases, in particular of the diseases mentioned above.

A further object of the present invention are the compounds according to the invention for use in a method for the treatment and/or prophylaxis of acute and chronic cardiac insufficiency, hypervolaemic and envolaemic hyponatraemia, liver cirrhosis, ascites, oedemas, and the syndrome of inadequate ADH secretion (SIADH).

A further object of the present invention is the use of the compounds according to the invention for the production of a medicament for the treatment and/or prophylaxis of diseases, in particular of the diseases mentioned above.

A further object of the present invention is a method for the treatment and/or prophylaxis of diseases, in particular of the diseases mentioned above, with the use of an effective quantity of at least one of the compounds according to the invention.

The compounds according to the invention can be used alone or if necessary in combination with other active substances. A further object of the present invention are medicaments which contain at least one of the compounds according to the invention and one or more other active substances, in particular for the treatment and/or prophylaxis of the diseases mentioned above. As combination active substances suitable for this, the following may for example and preferably be mentioned:
  organic nitrates and NO donors, such as for example sodium nitroprusside, nitroglycerine, isosorbide mononitrate, isosorbide dinitrate, molsidomine or SIN-1, and inhalational NO;
  diuretics, in particular loop diuretics and thiazides and thiazide-like diuretics;
  positive-inotropically active compounds, such as for example cardiac glycosides (digoxin), and beta-adrenergic and dopaminergic agonists such as isoproterenol, adrenalin, noradrenalin, dopamine and dobutamine;
  compounds which inhibit the degradation of cyclic guanosine monophosphate (cGMP) and/or cyclic adenosine monophosphate (cAMP), such as for example inhibitors of phosphodiesterases (PDE) 1, 2, 3, 4 and/or 5, in particular PDE 5 inhibitors such as sildenafil, vardenafil and tadalafil, and PDE 3 inhibitors such as amrinone and milrinone;
  natriuretic peptides such as for example "atrial natriuretic peptide" (ANP, anaritide), "B-type natriuretic peptide" or "brain natriuretic peptide" (BNP, nesiritide), "C-type natriuretic peptide" (CNP) and urodilatin;
  calcium sensitisers, such as for example and preferably levosimendan;
  NO- and haem-independent activators of guanylate cyclase, such as in particular the compounds described in WO 01/19355, WO 01/19776, WO 01/19778, WO 01/19780, WO 02/070462 and WO 02/070510;
  NO-independent, but haem-dependent stimulators of guanylate cyclase, such as in particular riociguat and the compounds described in WO 00/06568, WO 00/06569, WO 02/42301 and WO 03/095451;
  inhibitors of human neutrophil elastase (HNE), such as for example sivelestat or DX-890 (reltran);
  compounds inhibiting the signal transduction cascade, such as for example tyrosine kinase inhibitors, in particular sorafenib, imatinib, gefitinib and erlotinib;
  compounds influencing the energy metabolism of the heart, such as for example and preferably etomoxir, dichloroacetate, ranolazine or trimetazidine;
  agents with antithrombotic action, for example and preferably from the group of the thrombocyte aggregation inhibitors, anticoagulants or profibrinolytic substances;
  blood pressure-lowering active substances, for example and preferably from the group of the calcium antagonists, angiotensin AII antagonists, ACE inhibitors, vasopeptidase inhibitors, inhibitors of neutral endopeptidase, endothelin antagonists, renin inhibitors, alpha receptor blockers, beta receptor blockers, mineralocorticoid receptor antagonists and rho-kinase inhibitors; and/or
  active substances modifying fat metabolism, for example and preferably from the group of the thyroid receptor agonists, cholesterol synthesis inhibitors such as for example and preferably HMG-CoA reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric gallic acid adsorbers, gallic acid reabsorption inhibitors and lipoprotein(a) antagonists.

In a preferred embodiment of the invention, the compounds according to the invention are administered in combination with a diuretic, such as for example and preferably furosemid, bumetanid, torsemid, bendroflumethiazid, chlorthiazid, hydrochlorthiazid, hydroflumethiazid, methyclothiazid, polythiazid, trichlormethiazid, chlorthalidon, indapamid, metolazon, quinethazon, acetazolamid, dichlorophenamid, methazolamid, glycerine, isosorbide, mannitol, amilorid or triamteren.

Agents with antithrombotic action are understood preferably to mean compounds from the group of the thrombocyte aggregation inhibitors, anticoagulants or profibrinolytic substances.

In a preferred embodiment of the invention, the compounds according to the invention are administered in combination with a thrombocyte aggregation inhibitor, such as for example and preferably aspirin, clopidogrel, ticlopidine or dipyridamol.

In a preferred embodiment of the invention, the compounds according to the invention are administered in combination with a thrombin inhibitor, such as for example and preferably ximelagatran, melagatran, bivalirudin or clexane.

In a preferred embodiment of the invention, the compounds according to the invention are administered in combination with a GPIIb/IIIa antagonist, such as for example and preferably tirofiban or abciximab.

In a preferred embodiment of the invention, the compounds according to the invention are administered in combination with a factor Xa inhibitor, such as for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as for example and preferably coumarin.

Blood pressure-lowering agents are understood preferably to mean compounds from the group of the calcium antagonists, angiotensin AII antagonists, ACE inhibitors, vasopeptidase inhibitors, inhibitors of neutral endopeptidase, endothelin antagonists, renin inhibitors, alpha receptor blockers, beta receptor blockers, mineralocorticoid receptor antagonists, rho-kinase inhibitors and diuretics.

In a preferred embodiment of the invention, the compounds according to the invention are administered in combination with a calcium antagonist, such as for example and preferably nifedipin, amlodipin, verapamil or diltiazem.

In a preferred embodiment of the invention, the compounds according to the invention are administered in combination with an angiotensin AII antagonist, such as for example and preferably losartan, candesartan, valsartan, telmisartan or embusartan.

In a preferred embodiment of the invention, the compounds according to the invention are administered in combination with an ACE inhibitor, such as for example and preferably enalapril, captopril, lisinopril, ramipril, delapril, fosinopril, quinopril, perindopril or trandopril.

In a preferred embodiment of the invention, the compounds according to the invention are administered in combination with a vasopeptidase inhibitor or inhibitor of neutral endopeptidase (NEP), such as for example and preferably omapatrilat or AVE-7688.

In a preferred embodiment of the invention, the compounds according to the invention are administered in combination with an endothelin antagonist, such as for example and preferably bosentan, darusentan, ambrisentan or sitaxsentan.

In a preferred embodiment of the invention, the compounds according to the invention are administered in combination with a renin inhibitor, such as for example and preferably aliskiren, SPP-600 or SPP-800.

In a preferred embodiment of the invention, the compounds according to the invention are administered in combination with an alpha-1 receptor blocker, such as for example and preferably prazosin.

In a preferred embodiment of the invention, the compounds according to the invention are administered in combination with a beta receptor blocker, such as for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a mineralocorticoid receptor antagonist, such as for example and preferably spironolactone, eplerenon, canrenon or potassium canrenoate.

In a preferred embodiment of the invention, the compounds according to the invention are administered in combination with a rho-kinase inhibitor, such as for example and preferably fasudil, Y-27632, SLx-2119, BF-66851, BF-66852, BF-66853, KI-23095 or BA-1049.

Fat metabolism-modifying agents are understood preferably to mean compounds from the group of the CETP inhibitors, thyroid receptor agonists, cholesterol synthesis inhibitors such as HMG-CoA reductase or squalene synthesis inhibitors, ACAT inhibitors, MTP inhibitors, PPAR-alpha, PPAR-gamma and/or PPAR-delta agonists, cholesterol absorption inhibitors, polymeric gallic acid adsorbers, gallic acid reabsorption inhibitors, lipase inhibitors and lipoprotein (a) antagonists.

In a preferred embodiment of the invention, the compounds according to the invention are administered in combination with a CETP inhibitor, such as for example and preferably dalcetrapib, BAY 60-5521, anacetrapib or CETP-vaccine (CETi-1).

In a preferred embodiment of the invention, the compounds according to the invention are administered in combination with a thyroid receptor agonist, such as for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins, such as for example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as for example and preferably BMS-188494 or TAK-475.

In a preferred embodiment of the invention, the compounds according to the invention are administered in combination with an ACAT inhibitor, such as for example and preferably avasimibe, melinamide, pactimibe, eflucimibe or SMP-797.

In a preferred embodiment of the invention, the compounds according to the invention are administered in combination with an MTP inhibitor, such as for example and preferably implitapide, BMS-201038, R-103757 or JTT-130.

In a preferred embodiment of the invention, the compounds according to the invention are administered in combination with a PPAR-gamma agonist, such as for example and preferably pioglitazone or rosiglitazone.

In a preferred embodiment of the invention, the compounds according to the invention are administered in combination with a PPAR-delta agonist, such as for example and preferably GW-501516 or BAY 68-5042.

In a preferred embodiment of the invention, the compounds according to the invention are administered in combination with a cholesterol absorption inhibitor, such as for example and preferably ezetimibe, tiqueside or pamaqueside.

In a preferred embodiment of the invention, the compounds according to the invention are administered in combination with a lipase inhibitor, such as for example and preferably orlistat.

In a preferred embodiment of the invention, the compounds according to the invention are administered in combination with a polymeric gallic acid adsorber, such as for example and preferably cholestyramine, colestipol, colesolvam, cholestagel or colestimid.

In a preferred embodiment of the invention, the compounds according to the invention are administered in combination with a gallic acid reabsorption inhibitor, such as for example and preferably ASBT (=IBAT) inhibitors such as for example AZD-7806, S-8921, AK-105, BARI-1741, SC-435 or SC-635.

In a preferred embodiment of the invention, the compounds according to the invention are administered in combination with a lipoprotein(a) antagonist, such as for example and preferably gemcabene calcium (CI-1027) or nicotinic acid.

A further object of the present invention are medicaments which contain at least one compound according to the invention, usually together with one or more inert, non-toxic, pharmaceutically suitable additives, and the use thereof for the aforesaid purposes.

The compounds according to the invention can act systemically and/or locally. For this purpose, they can be administered in a suitable manner, such as for example by the oral, parenteral, pulmonary, nasal, sublingual, lingual, buccal, rectal, dermal, transdermal, conjunctival or aural routes or as an implant or stent.

For these administration routes, the compounds according to the invention can be administered in suitable administration forms.

For oral administration, administration forms which function according to the state of the art, releasing the compounds according to the invention rapidly and/or in a modified manner, which contain the compounds according to the invention in crystalline and/or amorphized and/or dissolved form, such as for example tablets (uncoated or coated tablets, for example with gastric juice-resistant or delayed dissolution or insoluble coatings, which control the release of the compound according to the invention), tablets rapidly disintegrating in the oral cavity or films/wafers, films/lyophilisates, capsules (for example hard or soft gelatine capsules), dragees, granules, pellets, powders, emulsions, suspensions, aerosols or solutions are suitable.

Parenteral administration can be effected omitting an absorption step (e.g. intravenous, intraarterial, intracardial, intraspinal or intralumbar administration) or involving absorption (e.g. intramuscular, subcutaneous, intracutaneous, percutaneous or intraperitoneal administration). Suitable administration forms for parenteral administration include injection and infusion preparations in the form of solutions, suspensions, emulsions, lyophilisates or sterile powders.

For the other administration routes, for example inhalation formulations (including powder inhalers and nebulisers), nasal drops, solutions or sprays, tablets for lingual, sublingual or buccal administration, tablets, films/wafers or capsules, suppositories, oral or ophthalmic preparations, vaginal capsules, aqueous suspensions (lotions, shakable mixtures), lipophilic suspensions, ointments, creams, transdermal therapeutic systems (e.g. plasters), milk, pastes, foams, dusting powders, implants or stents are suitable.

Oral or parenteral administration, in particular oral and intravenous administration, are preferred.

The compounds according to the invention can be converted into the stated administration forms. This can be effected in a manner known per se by mixing with inert, non-toxic, pharmaceutically suitable additives. These additives include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as for example ascorbic acid), colourants (e.g. inorganic pigments such as for example iron oxides) and flavour or odour correctors.

In general, to achieve effective results in parenteral administration it has been found advantageous to administer quantities of about 0.001 to 10 mg/kg, preferably about 0.01 to 1 mg/kg body weight. In oral administration, the dosage is about 0.01 bis 100 mg/kg, preferably about 0.01 to 20 mg/kg and quite especially preferably 0.1 to 10 mg/kg body weight.

Nonetheless it can sometimes be necessary to deviate from the said quantities, namely depending on body weight, administration route, individual response to the active substance, nature of the preparation and time or interval at which administration takes place. Thus in some cases it can be sufficient to manage with less than the aforesaid minimum quantity, while in other cases the stated upper limit must be exceeded. In the event of administration of larger quantities, it may be advisable to divide these into several individual administrations through the day.

The following practical examples illustrate the invention. The invention is not limited to the examples.

Unless otherwise stated, the percentages stated in the following tests and examples are percent by weight, parts are parts by weight, and solvent ratios, dilution ratios and concentration information about liquid/liquid solutions are each based on volume.

A. EXAMPLES

Abbreviations

Alk alkyl
Boc tert-butoxycarbonyl
Br.s broad singlet (in NMR)
CI chemical ionization (in MS)
DCI direct chemical ionization (in MS)
DME 1,2-dimethoxyethane
DMF dimethylformamide
DMSO dimethyl sulphoxide
EA ethyl acetate
EDC N(3-dimethylaminopropyl)-N-ethylcarbodiimide(hydrochloride)
eq. equivalent(s)
ESI electrospray ionization (in MS)
FMOC 9-fluorenylmethoxycarbonyl
GC/MS gas chromatography-coupled mass spectrometry
sat. saturated
h hour(s)
Hal halogen
HOBt 1-hydroxy-1H-benzotriazole hydrate
HPLC high pressure, high performance liquid chromatography
LC/MS liquid chromatography-coupled mass spectrometry
LDA lithium diisopropylamide
LiHMDS lithium hexamethyldisilazane
min(s) minute(s)
MS mass spectrometry
NMR nuclear magnetic resonance spectrometry
PG protective group
rac racemic/racemate
$R_f$ retention factor (in thin layer chromatography on silica gel)
RT room temperature
$R_t$ retention time (in HPLC)
TBTu O-(benzotriazol-1-yl)-N,N,N',N'-tetramethyluronium tetrafluoroborate
THF tetrahydrofuran
TMOF trimethyl orthoformate
UV ultraviolet spectrometry
v/v volume to volume ratio (of a solution)
LC/MS, HPLC and GC/MS Methods:
Method 1 (HPLC):
Instrument: HP 1100 with DAD detection; column: Kromasil RP-18, 150 mm×4.6 mm, 5 μm; Eluent A: 0.5 ml phosphoric acid (85% strength)/1 water, Eluent B: acetonitrile; gradient: 0 min 10% B, 1.0 min 10% B, 4.0 min 90% B, 5.0 min 90% B, 5.5 min 10% B, 6.0 min 10% B; flow rate: 2.0 ml/min; oven: 30° C.; UV detection: 210 nm.
Method 2 (LC/MS):
MS instrument type: Micromass ZQ; HPLC instrument type: Waters Alliance 2795; column: Phenomenex Synergi 2.5μ MAX-RP 100A Mercury 20 mm×4 mm; Eluent A: 1 l water+0.5 ml 50% formic acid, Eluent B: 1 l acetonitrile+0.5 ml 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 3 (LC/MS):

MS instrument type: Micromass ZQ; HPLC instrument type: HP 1100 Series; UV DAD; column: Phenomenex Gemini 3μ 30 mm×3.00 mm; Eluent A: 1 l water+0.5 ml 50% formic acid; Eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (LC/MS):

Instrument: Micromass Quattro Premier with Waters HPLC Acquity; column: Thermo Hypersil GOLD 1.9μ 50×1 mm; Eluent A: 1 l water+0.5 ml 50% formic acid, Eluent B: 1 l acetonitrile+0.5 ml 50% formic acid; gradient: 0.0 min 90% A→0.1 min 90% A→1.5 min 10% A→2.2 min 10% A; oven: 50° C.; flow rate: 0.33 ml/min; UV detection: 210 nm.

Method 5 (Preparative HPLC):

Instrument: Abimed Gilson Pump 305/306, Manometric Modulator 806; column: Grom-Sil 120 ODS-4HE 10 μm, 250 mm×30 mm; Eluent: A=water, B=acetonitrile; gradient: 0.0 min 10% B, 3 min 10% B, 30 min 95% B, 42 min 95% B, 42.01 min 10% B, 45 min 10% B; flow rate: 50 ml/min; column temperature: RT; UV detection: 210 nm.

Method 6 (LC/MS):

Instrument: Micromass Quattro Micro MS with HPLC Agilent Series 1100; column: Thermo Hypersil GOLD 3μ 20 mm×4 mm; Eluent A: 1 l water+0.5 ml 50% formic acid, Eluent B: 1 l acetonitrile+0.5 ml 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 7 (LC/MS):

MS instrument type: Waters ZQ; HPLC instrument type: Agilent 1100 Series; UV DAD; column: Thermo Hypersil GOLD 3μ 20 mm×4 mm; Eluent A: 1 l water+0.5 ml 50% formic acid, Eluent B: 1 l acetonitrile+0.5 ml 50% formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 8 (Preparative HPLC):

Column: Grom-Sil 120 ODS-4HE, 10 μm, 250 mm×30 mm; Eluent A: water, Eluent B: acetonitrile; gradient: 0.0 min 10% B→3 min 10% B→30 min 95% B→42 min 95% B→42.01 min 10% B→45 min 10% B; flow rate: 50 ml/min; column temperature: RT; UV detection: 210 nm.

Starting Compounds and Intermediates

Example 1A

2-[(4-Chlorophenyl)carbonyl]-N-(prop-2-ene-1-yl) hydrazinecarboxamide

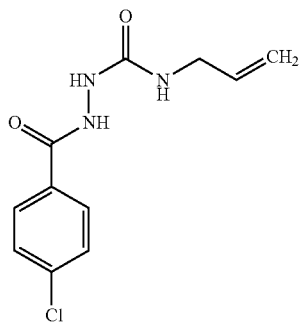 [SMILES: C=CCNC(=O)NNC(=O)c1ccc(Cl)cc1]

An amount of 5.00 g (29.3 mmol) of 4-chlorobenzenecarbohydrazide was suspended in dry tetrahydrofuran (150 ml) at 50° C. and then 2.63 ml (29.9 mmol) of allyl isocyanate in solution in 110 ml of dry tetrahydrofuran were added dropwise. The starting material underwent temporary complete dissolution, and then a fine precipitate was produced. The mixture was stirred at 50° C. for 2 hours. After cooling to room temperature it was admixed with diethyl ether. The colourless solid was isolated by suction filtration, washed with diethyl ether and dried in a high vacuum. This gave 7.42 g (100% of theory) of the target compound.

HPLC [Method 1] $R_t$=3.45 min

LC-MS [Method 3] $R_t$=1.51 min; MS [ESIpos]: m/z=254 $(M+H)^+$ $^1$H NMR (400 MHz, DMSO-$d_6$): δ=3.60-3.70 (m, 2H), 5.01 (dd, 1H), 5.14 (dd, 1H), 5.72-5.86 (m, 1H), 6.70 (s, 1H), 7.56 (d, 2H), 7.85-7.95 (m, 3H), 10.21 (s, 1H).

The compound below was obtained analogously:

| Example No. | Structure | LC/MS $R_t$ [Method] | HPLC $R_t$ [Method] |
|---|---|---|---|
| 2A | 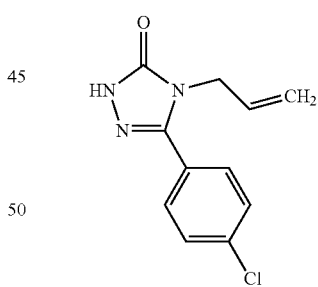 | $R_t$ = 0.71 min [4]; MS [ESIpos]: m/z = 254 $(M + H)^+$ | $R_t$ =3.332 min [1] |

Example 3A 5-(4-Chlorophenyl)-4-(prop-2-ene-1-yl)-2,4-dihydro-3H-1,2,4-triazol-3-one An amount of 26.8 g (106 mmol) of 2-[(4-chlorophenyl) carbonyl]-N-(prop-2-en-1-yl)hydrazinecarboxamide from Example 1A was suspended in 210 ml of 3M sodium hydroxide solution and heated under reflux for 20 hours. After cooling, a pH of 10 was set using half-concentrated hydrochloric acid. The colourless solid precipitated was isolated by suction filtration, washed to neutrality with water and then stirred up in methanol. The mixture was freed from insoluble constituents by filtration, the filtrate was concentrated under reduced pressure on a rotary evaporator and the residue was dried in a high vacuum. This gave 21.5 g (86.4% of theory) of the desired compound as a solid.

HPLC [Method 1] $R_t$=3.80 min;

LC-MS [Method 3] R$_t$=1.79 min; MS [ESIpos]: m/z=254 (M+H)$^+$ $^1$H NMR (400 MHz, DMSO-d$_6$): δ=4.30-4.35 (m, 2H), 4.91 (dd, 1H), 5.11 (dd, 1H), 5.76-5.90 (m, 1H), 7.58 (d, 2H), 7.65 (d, 2H), 12.05 (s, 1H).

The compound below was obtained analogously:

| Example No. | Structure | LC/MS R$_t$ [Method] | HPLC R$_t$ [Method] |
|---|---|---|---|
| 4A | 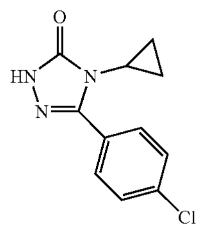 [SMILES: O=c1[nH]nc(-c2ccc(Cl)cc2)n1C1CC1] | R$_t$ = 1.85 min [3]; MS [ESIpos]: m/z = 236 (M + H)$^+$ | R$_t$ = 3.725 min [1] |

The synthesis of the following reactants is described in the cited patents.

| Example No. | Structure | Patent number Patent example [year] |
|---|---|---|
| 5A | | EP 703224 10 [1996] |
| 6A | | EP 422469 A2 II-36 [1991] |
| 7A | | EP 422469 A2 II-18 [1991] |
| 8A | | EP 422469 A2 II-27 [1991] |
| 9A | 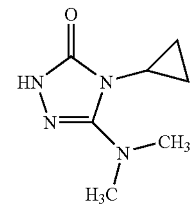 | EP 422469 A2 II-91 [1991] |
| 10A | 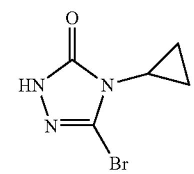 | EP 425948 II-3 [1991] |
| 11A | 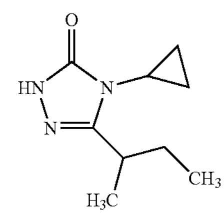 | EP 422469 A2 II-32 [1991] |
| 12A | 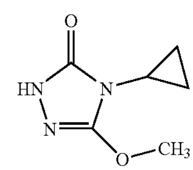 | EP 507171 II-5 [1992] |
| 13A | 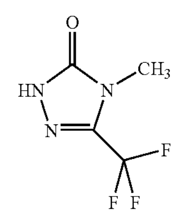 | US 3780052 2 [1973] |

Example 14A

4-{[3-(4-Chlorophenyl)-4-cyclopropyl-5-oxo-4,5-dihydro-1H-1,2,4-triazol-1-yl]sulphonyl}benzenecarbaldehyde An amount of 300 mg (1.27 mmol) of the compound from Example 4A was dissolved in 3 ml of DMF and admixed at 0° C. with 56 mg (1.40 mmol) of sodium hydride (60% in liquid paraffin). The mixture was stirred at this temperature for 30 minutes thereafter and then admixed with 260 mg (1.27 mmol) of 4-formylbenzenesulphonyl chloride. The mixture was warmed to room temperature and thereafter left with stirring at room temperature for 12 hours. The reaction mixture was admixed with 15 ml of water, and the precipitated solid was isolated by suction filtration, washed with a little water and dried in a high vacuum. This gave 351 mg (58% of theory) of the target compound.

LC-MS [Method 3]: $R_t$=2.36 min; MS [ESIpos]: m/z=404 (M+H)$^+$

Example 15A

4-{[3-(4-Chlorophenyl)-4-cyclopropyl-5-oxo-4,5-dihydro-1H-1,2,4-triazol-1-yl]sulphonyl}benzenecarboxylic acid

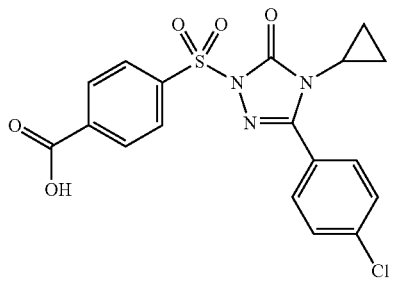 [SMILES: O=C(O)c1ccc(S(=O)(=O)n2nc(-c3ccc(Cl)cc3)n(C3CC3)c2=O)cc1]

An amount of 345 mg (0.73 mmol) of the compound from Example 14A and also 0.58 ml (5.45 mmol) of 2-methyl-2-butene were dissolved in 3 ml of acetone and admixed at RT with a solution of 376 mg (2.73 mmol) of sodium dihydrogenphosphate-1-hydrate and 460 mg (4.07 mmol) of sodium chlorite in 9 ml of water. The mixture was stirred at this temperature for 16 hours thereafter and then diluted with 15 ml of water and with 15 ml of ethyl acetate. After the phases had been separated, the aqueous phase was further extracted with 15 ml of ethyl acetate, and the combined organic phases were washed with saturated sodium chloride solution and dried over magnesium sulphate. Following filtration, the solvent was concentrated and the residue was dried in a high vacuum. This gave 337 mg (104% of theory) of the target compound, which was reacted further without additional purification.

LC/MS [Method 3]: $R_t$=2.28 min; MS [ESIpos]: m/z=419.9 (M+H)$^+$ $^1$H NMR (400 MHz, CDCl$_3$): δ=0.68-0.76 (m, 2H), 0.95-1.02 (m, 2H), 2.88 (m, 1H), 7.48 (d, 2H), 7.70 (d, 2H), 8.23 (s, 4H).

Example 16A

Ethyl N-({2-[(4-chlorophenyl)carbonyl]hydrazinyl}carbonyl)glycinate

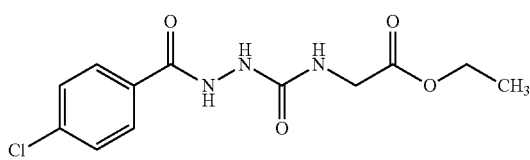 [SMILES: CCOC(=O)CNC(=O)NNC(=O)c1ccc(Cl)cc1]

A suspension of 12.95 g (75.9 mmol) of 4-chlorobenzohydrazide in 50 ml of dry THF was introduced at 50° C. and admixed dropwise with a solution of 10.0 g (77.5 mmol) of ethyl 2-isocyanatoacetate in 100 ml of dry THF. First of all a solution formed, and then a precipitate was produced. After the end of the addition, the mixture was stirred at 50° C. for 2 h more and then left to stand overnight at RT. The crystals were isolated by filtration, washed with a little diethyl ether and dried in a high vacuum. This gave 21.43 g (89% of theory) of the title compound.

LC/MS [Method 2]: $R_t$=1.13 min; m/z=300 (M+H)$^+$ $^1$H NMR (DMSO-d$_6$, 400 MHz): δ=1.19 (t, 3H), 3.77 (d, 2H), 4.09 (q, 2H), 6.88 (br. s, 1H), 7.57 (d, 2H), 7.91 (d, 2H), 8.21 (s, 1H), 10.29 (s, 1H).

Example 17A

[3-(4-Chlorophenyl)-5-oxo-1,5-dihydro-4H-1,2,4-triazol-4-yl]acetic acid

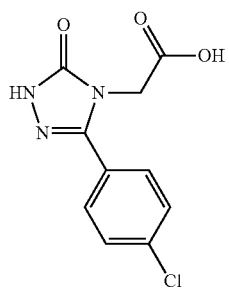 [SMILES: O=C(O)Cn1c(-c2ccc(Cl)cc2)n[nH]c1=O]

An amount of 21.43 g (67.9 mmol) of the compound from Example 16A was admixed with 91 ml of a 3 N sodium hydroxide solution and heated under reflux overnight. After cooling to RT, the mixture was adjusted to a pH of 1 by slow addition of approximately 20% strength hydrochloric acid. The precipitated solid was isolated by filtration, washed with water and dried at 60° C. under reduced pressure. This gave 17.55 g of the title compound in approximately 88% purity (90% of theory).

LC/MS [Method 2]: $R_t$=0.94 min; m/z=254 (M+H)$^+$ $^1$H NMR (DMSO-d$_6$, 400 MHz): δ=4.45 (s, 2H), 7.65-7.56 (m, 4H), 12.09 (s, 1H), 13.25 (br. s, 1H).

Example 18A 5-(4-Chlorophenyl)-4-(3,3,3-trifluoro-2-oxopropyl)-2,4-dihydro-3H-1,2,4-triazol-3-one (ketone form) or 5-(4-chlorophenyl)-4-(3,3,3-trifluoro-2,2-dihydroxypropyl)-2,4-dihydro-3H-1,2,4-triazol-3-one (hydrate form)

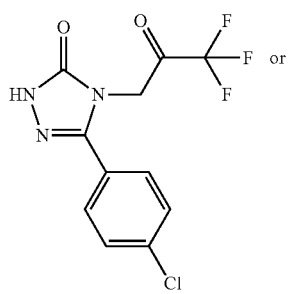

-continued

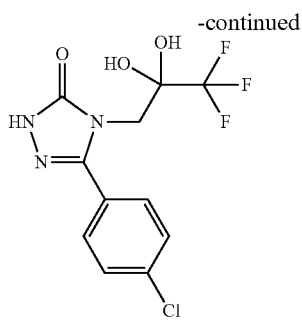

An amount of 5.0 g (16.36 mmol) of the compound from Example 17A was dissolved under argon in 200 ml of pyridine and admixed with 17.18 g (81.8 mmol) of trifluoroacetic anhydride. The temperature rose to about 35° C. After 30 min, the pyridine was removed on a rotary evaporator and the residue was admixed with 1.5 liters of 0.5N hydrochloric acid. This mixture was heated to 70° C. and then filtered while hot. The solid was washed with a little water. The entire filtrate was extracted three times with ethyl acetate. The combined organic phases were washed successively with water, with saturated aqueous sodium hydrogencarbonate solution and with saturated aqueous sodium chloride solution, dried over sodium sulphate and freed from the solvent on a rotary evaporator. The residue was dried in a high vacuum. This gave 3.56 g (68% of theory) of the title compound in the hydrate form.

LC/MS [Method 2]: $R_t$=1.51 min; m/z=306 (M+H)$^+$ and 324 (M+H)$^+$ (ketone form and hydrate form, respectively)

$^1$H NMR (DMSO-d$_6$, 400 MHz): δ=3.98 (s, 2H), 7.61 (d, 2H), 7.68 (br. s, 2H), 7.72 (d, 2H), 12.44 (s, 1H).

Example 19A 5-(4-Chlorophenyl)-4-(3,3,3-trifluoro-2-hydroxypropyl)-2,4-dihydro-3H-1,2,4-triazol-3-one

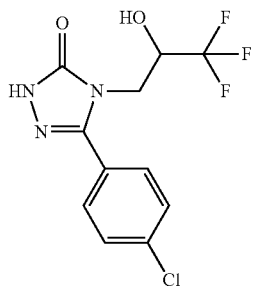 [SMILES: O=c1[nH]nc(-c2ccc(Cl)cc2)n1CC(O)C(F)(F)F]

An amount of 3.56 g (11.0 mmol) of the compound from Example 18A was dissolved in 100 ml of methanol and admixed, with ice cooling, with 3.75 g (99.5 mmol) of sodium borohydride. After 1.5 h, 200 ml of 1M hydrochloric acid were slowly added. The methanol was removed on a rotary evaporator and the residue was diluted with 500 ml of water and extracted three times with ethyl acetate. The combined organic phases were washed with saturated aqueous sodium hydrogencarbonate solution and then with saturated aqueous sodium chloride solution, dried over sodium sulphate and freed from the solvent on a rotary evaporator. The residue was dried in a high vacuum. This gave 3.04 g (90% of theory) of the title compound.

LC/MS [Method 6]: $R_t$=1.80 min; m/z=308 (M+H)$^+$ $^1$H NMR (DMSO-d$_6$, 400 MHz): δ=3.77 (dd, 1H), 3.92 (dd, 1H), 4.34-4.23 (m, 1H), 6.85 (d, 1H), 7.62 (d, 2H), 7.75 (d, 2H), 12.11 (s, 1H).

Example 20A

Methyl 4-{[3-(4-chlorophenyl)-4-cyclopropyl-5-oxo-4,5-dihydro-1H-1,2,4-triazol-1-yl]methyl}-3-methoxybenzenecarboxylate

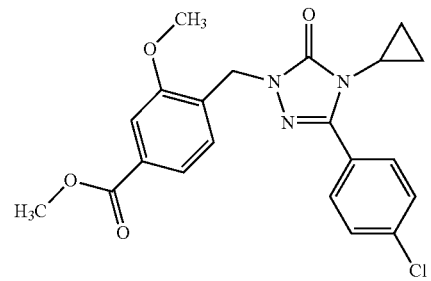 [SMILES: COC(=O)c1ccc(Cn2nc(-c3ccc(Cl)cc3)n(C3CC3)c2=O)c(OC)c1]

An amount of 800 mg (3.39 mmol) of 5-(4-chlorophenyl)-4-cyclopropyl-2,4-dihydro-3H-1,2,4-triazol-3-one (preparation as per WO 2007/134862 Example 36A) and 1.66 g (5.09 mmol) of caesium carbonate were suspended in 10 ml of acetone and admixed with 1.14 g (4.41 mmol) of methyl-4-(bromomethyl)-3-methoxybenzenecarboxylate. The mixture was stirred at 60° C. for 2 h. The suspension was diluted with water. It was extracted with twice 15 ml of ethyl acetate. The combined organic phases were dried over sodium sulphate and freed from the solvent on a rotary evaporator. Purification by flash chromatography over silica gel with elution with cyclohexane/ethyl acetate (gradient 4:1→1:1) gave 910 mg (64% of theory) of the target compound.

LC/MS [Method 4] $R_t$=1.28 min; MS [ESIpos]: m/z=414 (M+H)$^+$ $^1$H NMR (400 MHz, CDCl$_3$): δ=0.75-0.83 (m, 2H), 1.00-1.07 (m, 2H), 2.97-3.05 (m, 1H), 3.90 (s, 3H), 3.92 (s, 3H), 5.08 (s, 2H), 7.17 (d, 1H), 7.43 (d, 2H), 7.53 (s, 1H), 7.59 (d, 1H), 7.68 (d, 2H).

Example 21A

4-{[3-(4-Chlorophenyl)-4-cyclopropyl-5-oxo-4,5-dihydro-1H-1,2,4-triazol-1-yl]methyl}-3-methoxy-benzenecarboxylic acid

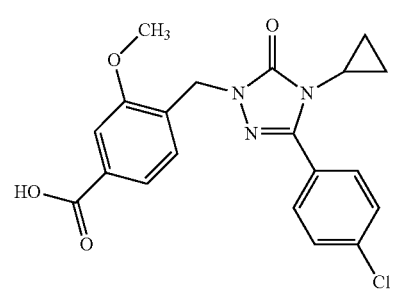 [SMILES: COc1cc(C(=O)O)ccc1Cn1nc(-c2ccc(Cl)cc2)n(C2CC2)c1=O]

An amount of 830 mg (2.01 mmol) of the compound from Example 20A was dissolved in 10 ml of tetrahydrofuran/ methanol (1:1) and admixed with 2 ml of a 2 N sodium hydroxide solution (4.01 mmol). The mixture was stirred at 80° C. for an hour. The reaction solution was diluted with 10 ml of water and extracted with twice 15 ml of ethyl acetate. The combined organic phases did not contain a product and were discarded. The aqueous product phase was acidified with 1 N hydrochloric acid and the resulting precipitate was isolated by filtration. The solid was dried in a high vacuum. Since the mother liquor still contained a large amount of product, it was concentrated completely on a rotary evaporator. This gave, all in all, 747 mg (93% of theory) of the target compound.

LC/MS [Method 4] $R_t$=1.11 min; MS [ESIpos]: m/z=400 (M+H)$^+$ $^1$H NMR (400 MHz, CDCl$_3$): δ=0.77-0.85 (m, 2H), 1.01-1.08 (m, 2H), 2.99-3.07 (m, 1H), 3.92 (s, 3H), 5.11 (s, 2H), 7.17 (d, 1H), 7.44 (d, 2H), 7.54 (s, 1H), 7.61 (d, 1H), 7.70 (d, 2H).

Example 22A

N-tert-Butyl-2-methoxy-4-methylbenzamide

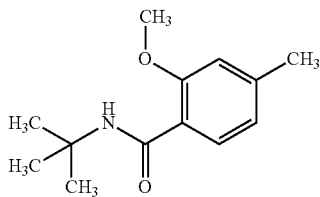 [SMILES: COc1cc(C)ccc1C(=O)NC(C)(C)C]

An amount of 200 mg (1.24 mmol) of 2-methoxy-4-benzoic acid was introduced in 3 ml of DMF and admixed with 240 mg (1.57 mmol) of HOBt and with 277 mg (1.44 mmol) of EDC. After 10 min of stirring at RT, 139 μl (1.32 mmol) of 2-methylpropan-2-amine were added and the mixture was stirred further at room temperature for 30 min. Subsequently the reaction solution was admixed with about 5 ml of water and extracted with twice 10 ml of ethyl acetate. The combined organic phases were dried over sodium sulphate, filtered and concentrated under reduced pressure. The crude product was purified by chromatography [Method 8]. This gave 164 mg (62% of theory) of the target compound.

LC/MS [Method 2] $R_t$=1.88 min; MS [ESIpos]: m/z=222 (M+H)$^+$

Example 23A 4-(Bromomethyl)-N-tert-butyl-2-methoxybenzamide

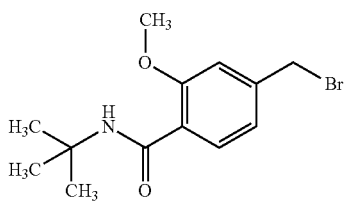 [SMILES: COc1cc(CBr)ccc1C(=O)NC(C)(C)C]

An amount of 160 mg (0.72 mmol) of the compound from Example 22A was heated under reflux with 129 mg (0.72 mmol) of N-bromosuccinimide and also 12 mg (0.07 mmol) of 2,2'-azobis-2-methylpropanenitrile in 5 ml of carbon tetrachloride for 16 h. After cooling to RT, the mixture was diluted with 10 ml of dichloromethane and washed with 10 ml of water. It was dried over sodium sulphate, filtered and concentrated under reduced pressure. The crude product was subsequently purified by chromatography [Method 8]. This gave 103 mg (47% of theory) of the target compound.

LC/MS [Method 7] $R_t$=2.32 min; MS [ESIpos]: m/z=300 and 302 (M+H)$^+$ $^1$H NMR (400 MHz, CDCl$_3$): δ=1.45 (s, 9H), 3.97 (s, 3H), 4.47 (s, 2H), 6.98 (d, 1H), 7.08 (dd, 1H), 7.75 (br. s., 1H), 8.14 (d, 1H).

Example 24A

Methyl 4-{[3-(4-chlorophenyl)-5-oxo-4-(3,3,3-trifluoro-2-hydroxypropyl)-4,5-dihydro-1H-1,2,4-triazol-1-yl]methyl}benzoate

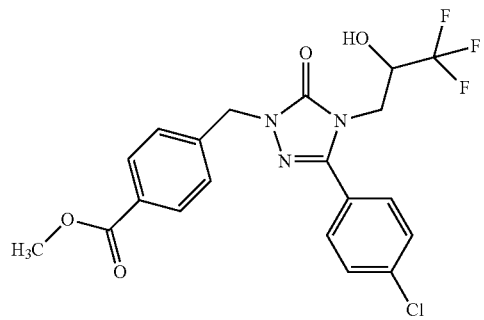 [SMILES: COC(=O)c1ccc(Cn2nc(-c3ccc(Cl)cc3)n(CC(O)C(F)(F)F)c2=O)cc1]

An amount of 305 mg (0.99 mmol) of the compound from Example 19A and 355 mg (1.09 mmol) of caesium carbonate were suspended in 10 ml of acetone and admixed with 227 mg (0.99 mmol) of methyl 4-(bromomethyl)benzoate. The mixture was stirred at 50° C. for 3 h. The suspension was diluted with water. It was extracted with twice 15 ml of ethyl acetate. The combined organic phases were dried over sodium sulphate and freed from the solvent on a rotary evaporator. Purification by flash chromatography over silica gel with elution with cyclohexane/ethyl acetate (gradient 10:1→2:1) gave 284 mg (63% of theory) of the target compound.

LC/MS [Method 4] $R_t$=1.28 min; MS [ESIpos]: m/z=456 (M+H)$^+$ $^1$H NMR (400 MHz, CDCl$_3$): δ=3.91 (s, 3H), 3.98-4.13 (m, 2H), 4.41-4.51 (m, 1H), 4.91 (d, 1H), 5.07 (s, 2H), 7.45 (d, 2H), 7.46-7.53 (m, 4H), 8.03 (d, 2H).

Example 25A

Methyl 3-{[3-(4-chlorophenyl)-5-oxo-4-(3,3,3-trifluoro-2-hydroxypropyl)-4,5-dihydro-1H-1,2,4-triazol-1-yl]methyl}benzoate

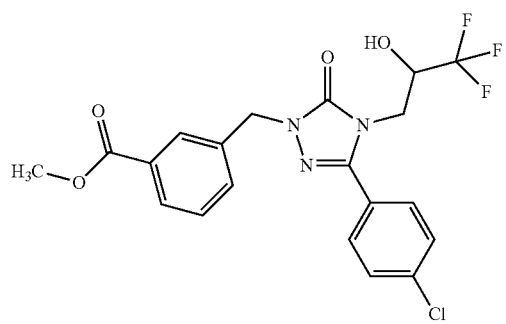 [SMILES: COC(=O)c1cccc(Cn2nc(-c3ccc(Cl)cc3)n(CC(O)C(F)(F)F)c2=O)c1]

In the same way as for the compound from Example 24A, 267 mg (0.87 mmol) of the compound from Example 19A were reacted with 199 mg (0.87 mmol) of methyl 3-(bromomethyl)benzoate. This gave 302 mg (76% of theory) of the target compound.

LC/MS [Method 7] R$_t$=2.41 min; MS [ESIpos]: m/z=456 (M+H)$^+$ $^1$H NMR (400 MHz, CDCl$_3$): δ=3.91 (s, 3H), 4.01 (dd, 1H), 4.09 (dd, 1H), 4.45-4.57 (m, 1H), 5.02-5.17 (m, 3H), 7.41-7.55 (m, 4H), 7.58 (d, 1H), 7.93 (s, 1H), 7.98 (d, 1H).

Example 26A tert-Butyl-3-chloro-4-{[3-(4-chlorophenyl)-4-cyclopropyl-5-oxo-4,5-dihydro-1H-1,2,4-triazol-1-yl]methyl}benzoate

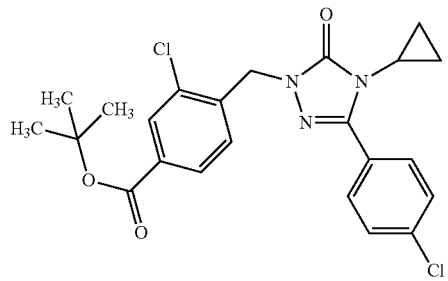 [SMILES: CC(C)(C)OC(=O)c1ccc(Cn2nc(-c3ccc(Cl)cc3)n(C3CC3)c2=O)c(Cl)c1]

An amount of 1.00 g (4.22 mmol) of 5-(4-chlorophenyl)-4-cyclopropyl-2,4-dihydro-3H-1,2,4-triazol-3-one (preparation as per WO 2007/134862 Example 36A) and 2.07 g (6.37 mmol) of caesium carbonate were suspended in 15 ml of acetone and admixed with 1.69 g (5.52 mmol) of tert-butyl-4-(bromomethyl)-3-chlorobenzoate (preparation as per WO 2003/000692, Example 4b). The mixture was stirred at 50° C. for 18 h. The suspension was diluted with water. It was extracted with twice 15 ml of ethyl acetate. The combined organic phases were dried over sodium sulphate and freed from the solvent on a rotary evaporator. Purification by flash chromatography over silica gel with elution with cyclohexane/ethyl acetate (gradient 9:1→3:2) gave 1.41 g (53% of theory) of the target compound in a purity of 74%.

LC/MS [Method 7] R$_t$=2.98 min; MS [ESIpos]: m/z=460 (M+H)$^+$ $^1$H NMR (400 MHz, CDCl$_3$): δ=0.75-0.83 (m, 2H), 1.00-1.09 (m, 2H), 1.57 (s, 9H), 3.01 (spt, 1H), 5.16 (s, 2H), 7.24-7.28 (m, 1H), 7.41-7.47 (m, 2H), 7.65-7.71 (m, 2H), 7.84 (dd, 1H), 7.98 (d, 1H).

Example 27A

3-Chloro-4-{[3-(4-chlorophenyl)-4-cyclopropyl-5-oxo-4,5-dihydro-1H-1,2,4-triazol-1-yl]methyl}benzoic acid

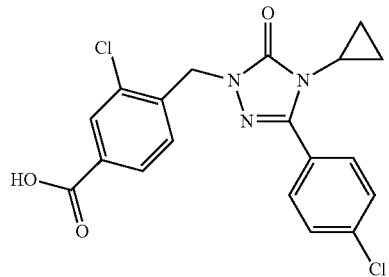 [SMILES: O=C(O)c1ccc(Cn2nc(-c3ccc(Cl)cc3)n(C3CC3)c2=O)c(Cl)c1]

An amount of 1.38 g (3.00 mmol) of the compound from Example 26A was dissolved in 10 ml of dichloromethane and admixed at RT with 3.0 ml (39 mmol) of trifluoroacetic acid and stirred at RT for 72 h. The mixture was concentrated under reduced pressure and admixed with 10 ml of toluene and concentrated again. This procedure was repeated a further two times. The residue which remained was freed from remnants of solvent under a high vacuum. This gave 1.27 g (63% of theory) of the target compound with a purity of 60%.

LC/MS {Method 2] R$_t$=1.85 min; MS [ESIpos]: m/z=404 (M+H)$^+$

Example 28A

4-{[3-(4-Chlorophenyl)-5-oxo-4-(3,3,3-trifluoro-2-hydroxypropyl)-4,5-dihydro-1H-1,2,4-triazol-1-yl]methyl}benzoic acid

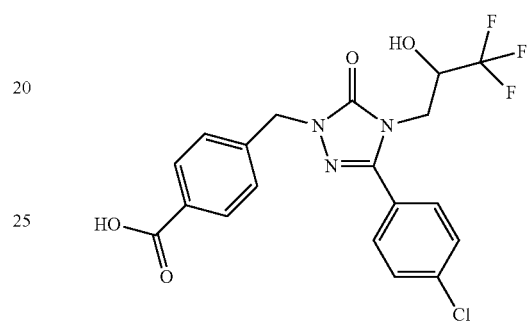

An amount of 280 mg (0.61 mmol) of the compound from Example 24A was dissolved in 4 ml of a 1:1 mixture of methanol and THF and admixed with 0.61 ml of 2 N sodium hydroxide solution. It was stirred at 80° C. for 1 h. For working out, it was admixed with 5 ml of water and extracted with 5 ml of ethyl acetate. The aqueous phase was acidified to a pH of 1 using 1 N hydrochloric acid and extracted with twice 5 ml of ethyl acetate. The combined organic phases were dried over sodium sulphate and freed from the solvent on a rotary evaporator. This gave 275 mg (100% of theory) of the target compound.

LC/MS [Method 7] R$_t$=2.14 min; MS [ESIpos]: m/z=442 (M+H)$^+$ $^1$H NMR (400 MHz, DMSO-d$_6$): δ=3.84 (dd, 1H), 3.96-4.03 (m, 1H), 4.24-4.36 (m, 1H), 5.08 (s, 2H), 7.42 (d, 2H), 7.60-7.64 (m, 2H), 7.75 (d, 2H), 7.93 (d, 2H).

Example 29A

3-{[3-(4-Chlorophenyl)-5-oxo-4-(3,3,3-trifluoro-2-hydroxypropyl)-4,5-dihydro-1H-1,2,4-triazol-1-yl]methyl}benzoic acid

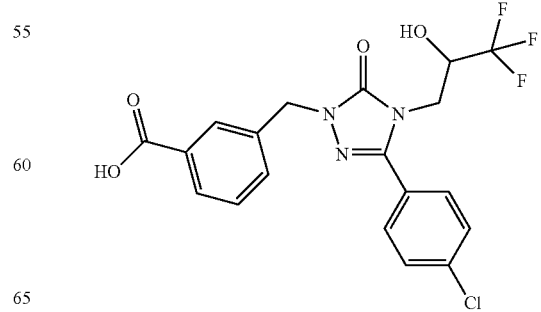

In the same way as for the compound from Example 28A, 265 mg (0.58 mmol) of the compound from Example 25A were reacted. This gave 250 mg (97% of theory) of the target compound.

LC/MS [Method 7] $R_t$=2.41 min; MS [ESIpos]: m/z=456 (M+H)$^+$ $^1$H NMR (400 MHz, DMSO-d$_6$): δ=3.84 (dd, 1H), 4.00 (dd, 1H), 4.23-4.34 (m, 1H), 5.00-5.13 (m, 2H), 7.46-7.53 (m, 1H), 7.54-7.59 (m, 1H), 7.60-7.64 (m, 2H), 7.74 (d, 2H), 7.88 (d, 1H), 7.94 (s, 1H).

Embodying Examples

Example 1

N-tert-Butyl-4-{[3-(4-chlorophenyl)-5-oxo-4-prop-2-en-1-yl-4,5-dihydro-1H-1,2,4-triazol-1-yl]sulpho-nyl}-3-methoxybenzenecarboxamide

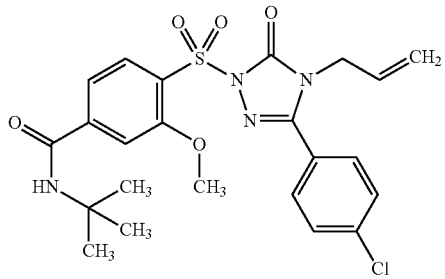 [SMILES: C=CCn1c(-c2ccc(Cl)cc2)nn(S(=O)(=O)c2ccc(C(=O)NC(C)(C)C)cc2OC)c1=O]

An amount of 231 mg (0.24 mmol) of the compound from Example 3A was suspended in 4 ml of tetrahydrofuran and cooled to −78° C. This suspension was admixed with stirring with 110 mg (0.981 mmol) of potassium tert-butylate. The mixture was allowed to warm to room temperature, and the solid dissolved. The reaction solution was stirred at room temperature for 10 minutes thereafter. Subsequently it was cooled again to −78° C. It was admixed with 300 mg (0.981 mmol) of 4-(tert-butylcarbamoyl)-2-methoxybenzene-sulphonyl chloride (illustration as per Liotta et al., *J. Org. Chem.*, 2001, 66, 3653-3661), the cooling bath was removed, and the solution was left with further stirring at room temperature overnight. The residue was admixed with water. It was extracted twice with ethyl acetate. The combined organic phases were dried over sodium sulphate and freed from the solvent on a rotary evaporator. The residue was purified by preparative HPLC (Method 6). This gave 275 mg (55% of theory) of the target compound.

LC/MS [Method 4]: $R_t$=1.29 min; MS [ESIpos]: m/z=505 (M+H)$^+$ $^1$H NMR (400 MHz, CDCl$_3$): δ=1.47 (s, 9H), 3.94 (s, 3H), 4.27-4.31 (m, 2H), 5.07 (d, 1H), 5.27 (d, 1H), 5.77-5.89 (m, 1H), 5.99 (s, NH), 7.22-7.28 (m, 1H), 7.41-7.46 (m, 2H), 7.49-7.55 (m, 3H), 8.16 (d, 1H).

The compounds below were obtained analogously:

| Example No. | Structure | Reactant; yield [% of theory] | $^1$H NMR (400 MHz, CDCl$_3$) LC/MS: $R_t$ [Method] |
|---|---|---|---|
| 2 | 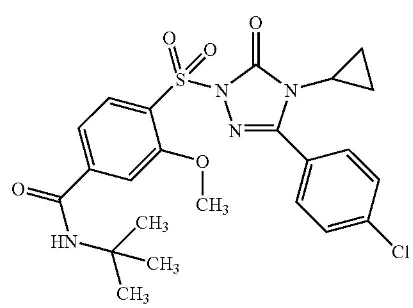 [SMILES: COc1cc(C(=O)NC(C)(C)C)ccc1S(=O)(=O)n1nc(-c2ccc(Cl)cc2)n(C2CC2)c1=O] | 4A; 49% | δ = 0.69-0.75 (m, 2H), 0.97-1.03 (m, 2H), 1.47 (s, 9H), 2.90 (m, 1H), 3.93 (s, 3H), 5.98 (br. s, 1H), 7.22-7.26 (m, 1H), 7.46 (d, 2H), 7.51 (s, 1H), 7.68 (d, 2H), 8.16 (d, 1H). LC-MS [3]: $R_t$ = 2.47 min; MS [ESIpos]; m/z = 505 (M + H)$^+$ |
| 3 | 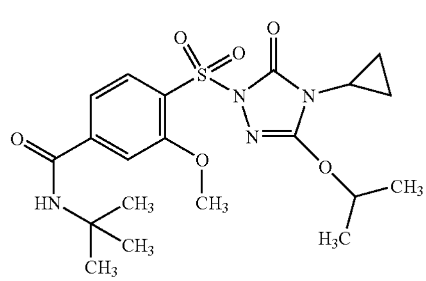 [SMILES: COc1cc(C(=O)NC(C)(C)C)ccc1S(=O)(=O)n1nc(OC(C)C)n(C2CC2)c1=O] | 5A; 78% | δ = 0.91-0.99 (m, 4H), 1.31 (s, 3H), 1.32 (s, 3H), 1.48 (s, 9H), 2.58-2.64 (m, 1H), 3.93 (s, 3H), 4.95-5.05 (m, 1H), 6.01 (br. s, 1H), 7.22 (dd, 1H), 7.50 (s, 1H), 8.08 (d, 1H), LC-MS [3]: $R_t$ = 2.26 min; MS [ESIpos]: m/z = 453 (M + H)$^+$ |

| Example No. | Structure | Reactant; yield [% of theory] | ¹H NMR (400 MHz, CDCl₃) LC/MS: $R_t$ [Method] |
|---|---|---|---|
| 4 | 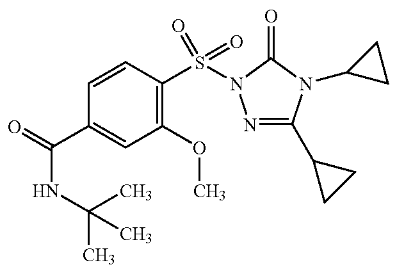 [SMILES: COc1cc(C(=O)NC(C)(C)C)ccc1S(=O)(=O)n1nc(C2CC2)n(C2CC2)c1=O] | 6A; 53% | δ = 0.98-1.11 (m, 8H), 1.47 (s, 9H), 1.81-1.90 (m, 1H), 2.71-2.78 (m,1H), 3.91 (s, 3H), 6.01 (br. s, 1H), 7.22 (dd, 1H), 7.48 (s, 1H), 8.08 (d, 1H). LC-MS [3]: $R_t$ = 2.08 min; MS [ESIpos]: m/z = 435 (M + H)⁺ |
| 5 | 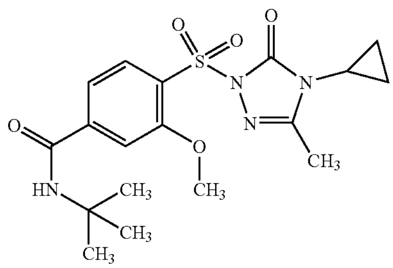 [SMILES: COc1cc(C(=O)NC(C)(C)C)ccc1S(=O)(=O)n1nc(C)n(C2CC2)c1=O] | 7A; 57% | δ = 0.94-1.00 (m, 2H), 1.00-1.09 (m, 2H), 1,47 (s, 9H), 2.29 (s, 3H), 2.63-2.70 (m, 1H), 3.93 (s, 3H), 5.99 (br. s, 1H), 7.23 (d, 1H), 7.50 (s, 1H) 8.12 (d, 1H). LC-MS [5]: $R_t$ = 0.97 min; MS [ESIpos]: m/z = 409 (M + H)⁺ |
| 6 | 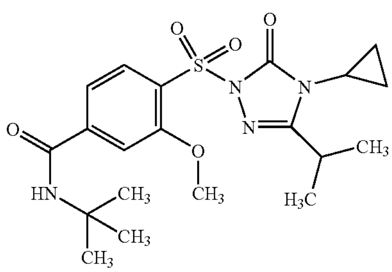 [SMILES: COc1cc(C(=O)NC(C)(C)C)ccc1S(=O)(=O)n1nc(N(C)C)n(C2CC2)c1=O] | 8A; 66% | δ = 0.96-1.09 (m, 4H), 1.30 (d, 6H), 1.47 (s, 9H), 2.60-2.68 (m,1H), 2.99-3.11 (m, 1H), 3.91 (s, 3H), 6.00 (br. s, 1H), 7.23 (d, 1H), 7.49 (s, 1H), 8.12 (d, 1H). LC-MS [5]: $R_t$ = 1.12 min; MS [ESIpos]: m/z 437 (M + H)⁺ |
| 7 | 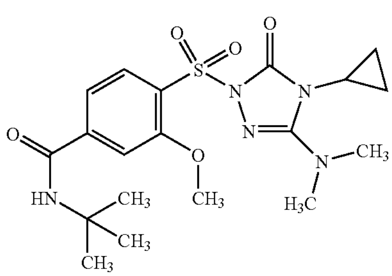 | 9A; 67% | δ = 0.95-1.02 (m, 2H), 1.02-1.11 (m, 2H), 1.48 (s, 9H), 2.67-2.74 (m, 1H), 2.85 (s, 6H), 3.93 (s, 3H), 6.04 (br. s, 1H), 7.23 (dd, 1H), 7.49 (d, 1H), 8.07 (d, 1H). LC-MS [2]: $R_t$ = 1.56 min; MS [ESIpos]: m/z = 438 (M + H)⁺ |
| 8 | 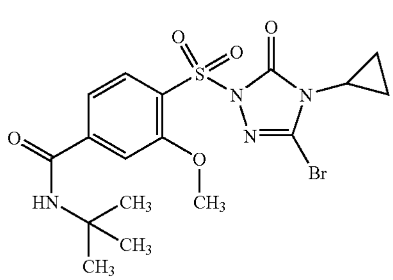 [SMILES: COc1cc(C(=O)NC(C)(C)C)ccc1S(=O)(=O)n1nc(Br)n(C2CC2)c1=O] | 10A; 80% | δ = 1.01-1.14 (m, 4H), 1.48 (s, 9H), 2.67-2.74 (m, 1H), 3.95 (s, 3H), 5.98 (br. s, 1H), 7.24 (dd, 1H), 7.52 (d, 1H), 8.11 (d, 1H). LC-MS [2]: $R_t$ = 1.71 min; MS [ESIpos]: m/z = 473 (M + H)⁺ |

-continued

| Example No. | Structure | Reactant; yield [% of theory] | ¹H NMR (400 MHz, CDCl₃) LC/MS: $R_t$ [Method] |
|---|---|---|---|
| 9 | 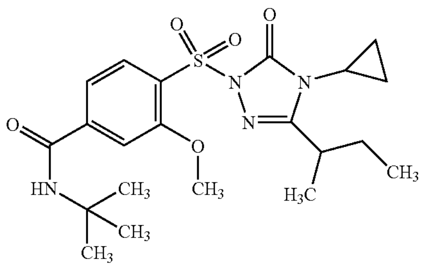 | 11A; 68% | δ = 0.88 (t, 3H), 0.94-1.09 (m, 4H), 1.27 (d, 3H), 1.47 (s, 9H), 1.54-1.67 (m,1H), 1.75-1.88 (m, 1H), 2.58-2.65 (m, 1H), 2.84-2.94 (m, 1H), 3.90 (s, 3H), 6.00 (br. s, 1H), 7.23 (dd, 1H), 7.49 (d, 1H), 8.12 (d, 1H). LC-MS [3]: $R_t$ = 2.28 min; MS [ESIpos]: m/z = 251 (M + H)⁺ |
| 10 | 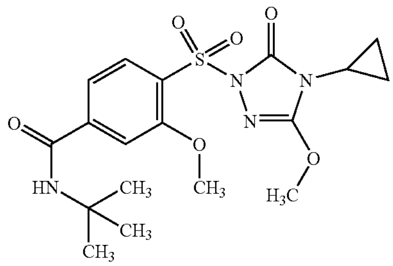 [SMILES: COc1cc(C(=O)NC(C)(C)C)ccc1S(=O)(=O)n1nc(OC)n(C2CC2)c1=O] | 12A; 73% | δ = 0.92-1.02 (m, 4H), 1.48 (s, 9H), 2.59-2.66 (m, 1H), 3.94 (s, 3H), 3.95 (s, 3H), 6.01 (br. s, 1H), 7.23 (dd, 1H), 7.50 (d, 1H), 8.08 (d, 1H). LC-MS [3]: $R_t$ = 2.01 min; MS [ESIpos]: m/z = 425 (M + H)⁺ |
| 11 | 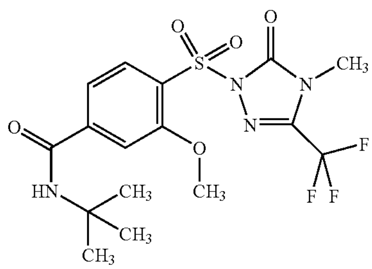 [SMILES: COc1cc(C(=O)NC(C)(C)C)ccc1S(=O)(=O)n1nc(C(F)(F)F)n(C)c1=O] | 13A; 55% | δ = 1.48 (s, 9H), 3.35 (s, 3H), 3.94 (s, 3H), 5.98 (br. s, 1H), 7.26 (dd, 1H), 7.53 (d, 1H), 8.15 (d, 1H). LC-MS [4]: $R_t$ = 1.14 min; MS [ESIpos]: m/z = 437 (M + H)⁺ |
| 12 | 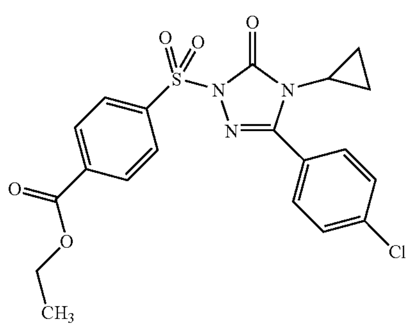 [SMILES: CCOC(=O)c1ccc(S(=O)(=O)n2nc(-c3ccc(Cl)cc3)n(C3CC3)c2=O)cc1] | 4A; 19% | δ = 0.68-0.76 (m, 2H) 0.95-1.03 (m, 2H), 1.40 (t, 3H), 2.82-2.89 (m, 1H), 4.42 (q, 2H), 7.46 (d, 2H), 7.68 (d, 2H), 8.19-8.25 (m, 4H). LC-MS [3]: $R_t$ = 2.70 min; MS [ESIpos]: m/z = 448 (M + H)⁺ |
| 13 | 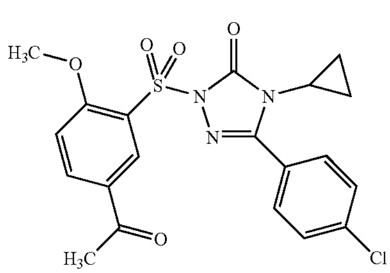 [SMILES: COc1ccc(C(C)=O)cc1S(=O)(=O)n1nc(-c2ccc(Cl)cc2)n(C2CC2)c1=O] | 4A; 16% | δ = 0.71-0.78 (m, 2H), 0.98-1.06 (m, 2H), 2.63 (s, 3H), 2.87-2.95 (m, 1H), 3.97 (s, 3H), 7.08 (d, 1H), 7.46 (d, 2H), 7.70 (d, 2H), 8.28 (dd, 1H), 8.28 (d, 1H). LC-MS [3]: $R_t$ = 2.30 min; MS [ESIpos]: m/z = 448 (M + H)⁺ |

Example 14

N-tert-Butyl-4-{[3-(4-chlorophenyl)-5-oxo-4,5-dihydro-1H-1,2,4-triazol-1-yl]sulphonyl}-3-methoxybenzenecarboxamide

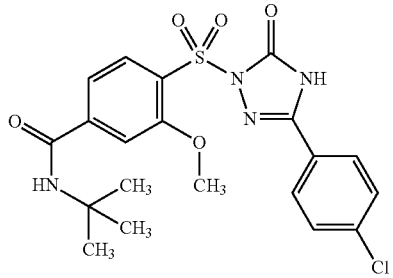 [SMILES: COc1cc(C(=O)NC(C)(C)C)ccc1S(=O)(=O)n1nc(-c2ccc(Cl)cc2)[nH]c1=O]

An amount of 194 mg (0.384 mmol) of N-tert-butyl-4-{[3-(4-chlorophenyl)-5-oxo-4-prop-2-en-1-yl-4,5-dihydro-1H-1,2,4-triazol-1-yl]sulphonyl}-3-methoxybenzenecarboxamide from Example 1 was dissolved under argon in 2 ml of degassed dioxane and admixed with 18 mg (0.015 mmol) of tetrakis(triphenylphosphine)palladium(0), 29 μl (0.77 mmol) of formic acid and 134 μl (0.96 mmol) of triethylamine. The mixture was stirred under reflux for 2 h. The dioxane was concentrated on a rotary evaporator and the residue in the flask was taken up in methanol. It was filtered over kieselguhr, the solid product was washed with methanol and the solvent was removed on a rotary evaporator. Ethyl acetate was added to the residue in the flask. Washing with water was carried out twice. The organic phase was dried over sodium sulphate and freed from the solvent on a rotary evaporator. Purification of the residue by flash chromatography on silica gel (solvent gradient cyclohexane/ethyl acetate 1:1 to ethyl acetate 100%) gave 152 mg (85% of theory) of the target compound.

LC/MS [Method 4] $R_t$=1.16 min; MS [ESIpos]: m/z=465 (M+H)$^+$ $^1$H NMR (400 MHz, CDCl$_3$): δ=1.47 (s, 9H), 3.86 (s, 3H), 6.02 (s, NH), 7.24-7.28 (m, 1H), 7.42 (d, 2H), 7.47 (s, 1H), 7.77 (d, 2H), 8.13 (d, 1H).

Example 15

Methyl 3-{[1-{[4-(tert-butylcarbamoyl)-2-methoxyphenyl]sulphonyl}-3-(4-chlorophenyl)-5-oxo-1,5-dihydro-4H-1,2,4-triazol-4-yl]methyl}benzenecarboxylate

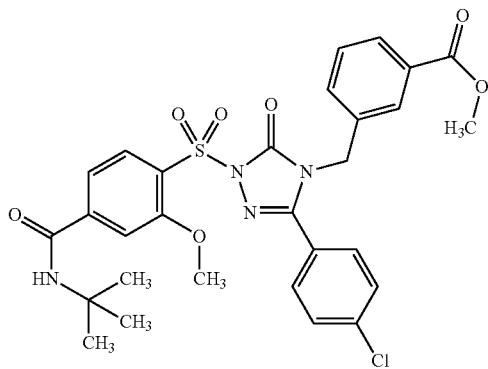 [SMILES: COC(=O)c1cccc(Cn2c(-c3ccc(Cl)cc3)nn(S(=O)(=O)c3ccc(C(=O)NC(C)(C)C)cc3OC)c2=O)c1]

An amount of 50 mg (0.108 mmol) of N-tert-butyl-4-{[3-(4-chlorophenyl)-5-oxo-4,5-dihydro-1H-1,2,4-triazol-1-yl]sulphonyl}-3-methoxybenzenecarboxamide from Example 14 and 53 mg (0.161 mmol) of caesium carbonate was suspended in 1 ml of dimethylformamide and admixed with 32 mg (0.140 mmol) of methyl 3-bromomethylbenzoate. The mixture was stirred at 60° C. overnight. The suspension was diluted with water. It was extracted twice with ethyl acetate. The combined organic phases were dried over sodium sulphate and freed from the solvent on a rotary evaporator. The crude product was purified by preparative HPLC [Method 5]. This gave 40 mg (60% of theory) of the target compound.

LC/MS [Method 3] $R_t$=2.67 min; MS [ESIpos]: m/z=613 (M+H)$^+$ $^1$H NMR (400 MHz, CDCl$_3$): δ=1.48 (s, 9H), 3.90 (s, 3H), 3.91 (s, 3H), 4.89 (s, 2H), 5.99 (s, NH), 7.24-7.27 (m, 1H), 7.28-7.34 (m, 3H), 7.38-7.42 (m, 3H), 7.54 (d, 1H), 7.67 (s, 1H), 7.97 (d, 1H), 8.17 (d, 1H).

Example 16

N-tert-Butyl-4-{[3-(4-chlorophenyl)-5-oxo-4-(3,3,3-trifluoro-2-hydroxypropyl)-4,5-dihydro-1H-1,2,4-triazol-1-yl]sulphonyl}-3-methoxybenzenecarboxamide

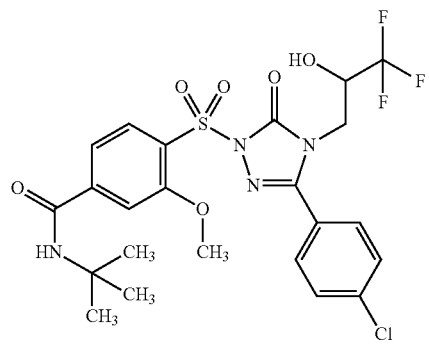 [SMILES: COc1cc(C(=O)NC(C)(C)C)ccc1S(=O)(=O)n1nc(-c2ccc(Cl)cc2)n(CC(O)C(F)(F)F)c1=O]

An amount of 50 mg (0.108 mmol) of N-tert-butyl-4-{[3-(4-chlorophenyl)-5-oxo-4,5-dihydro-1H-1,2,4-triazol-1-yl]sulphonyl}-3-methoxybenzenecarboxamide from Example 14 and 53 mg (0.161 mmol) of caesium carbonate were suspended in 1 ml of dimethylformamide and admixed with 26 μl (0.161 mmol) of 3-bromo-1,1,1-trifluoro-2-propanol. The mixture was stirred at 75° C. for 8 hours. The suspension was diluted with saturated aqueous ammonium chloride solution. It was extracted twice with ethyl acetate. The combined organic phases were dried over sodium sulphate and freed from the solvent on a rotary evaporator. The crude product was purified by preparative HPLC [Method 5]. This gave 22 mg (36% of theory) of the target compound.

LC/MS [Method 4] $R_t$=1.30 min; MS [ESIpos]: m/z=577 (M+H)$^+$ $^1$H NMR (400 MHz, CDCl$_3$): δ=1.47 (s, 9H), 3.87-3.97 (m, 2H), 3.96 (s, 3H), 4.40-4.59 (s, 2H), 6.04 (s, NH), 7.21-7.28 (m, 1H), 7.44-7.52 (m, 3H), 7.60 (d, 2H), 8.12 (d, 1H).

Example 17

N-tert-Butyl-4-{[3-(4-chlorophenyl)-4-cyclopropyl-5-oxo-4,5-dihydro-1H-1,2,4-triazol-1-yl]sulphonyl}benzenecarboxamide

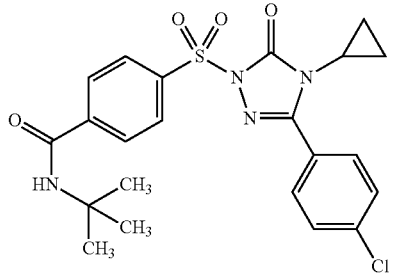 [SMILES: CC(C)(C)NC(=O)c1ccc(S(=O)(=O)n2nc(-c3ccc(Cl)cc3)n(C3CC3)c2=O)cc1]

An amount of 50 mg (0.113 mmol) of the compound from Example 15A was introduced in 1 ml of DMF and admixed with 18 mg (0.136 mmol) of 1-hydroxy-1H-benzotriazole hydrate and with 28 mg (0.147 mmol) of N'-(3-dimethylaminopropyl)-N-ethylcarbodiimide hydrochloride. After 10 minutes of stirring at RT, 2-methylpropan-2-amine (13.1 µl, 0.124 mmol) was added and the mixture was stirred further at room temperature overnight. Subsequently the reaction solution was diluted with methanol and purified by preparative HPLC [Method 5]. This gave 13 mg (24% of theory) of the target compound.

LC/MS [Method 3]: $R_t$=2.53 min; MS [ESIpos]: m/z=475 (M+H)$^+$ $^1$H NMR (400 MHz, CDCl$_3$): δ=0.68-0.74 (m, 2H), 0.94-1.02 (m, 2H), 1.47 (s, 9H), 2.85 (dt, 1H), 5.93 (br. s., 1H), 7.46 (d, 2H), 7.67 (d, 2H), 7.87 (d, 2H), 8.19 (d, 2H).

The compounds below were obtained analogously:

Example 20

N-tert-Butyl-4-{[3-(4-chlorophenyl)-4-cyclopropyl-5-oxo-4,5-dihydro-1H-1,2,4-triazol-1-yl]methyl}-3-methoxybenzenecarboxamide

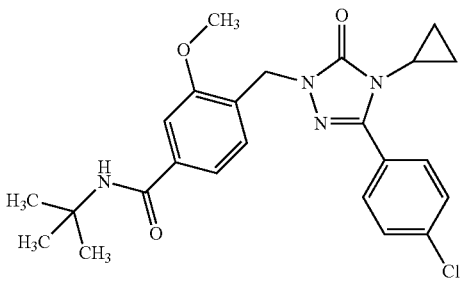

An amount of 50 mg (0.13 mmol) of the compound from Example 21A was introduced in 1 ml of DMF and admixed with 20 mg (0.15 mmol) of HOBt and with 31 mg (0.16 mmol) of EDC. After 10 minutes of stirring at RT, 14.5 µl (0.14 mmol) of 2-methylpropan-2-amine were added and the mixture was stirred further at room temperature for 16 h. Subsequently the reaction solution was diluted with about 5 ml of water and the precipitate formed was filtered and washed with water. Drying under reduced pressure gave 37 mg (66% of theory) of the target compound.

LC/MS [Method 2] $R_t$=2.03 min; MS [ESIpos]: m/z=455 (M+H)$^+$ $^1$H NMR (400 MHz, CDCl$_3$): δ=0.74-0.80 (m, 2H), 0.99-1.06 (m, 2H), 1.46 (s, 9H), 2.96-3.03 (m, 1H), 3.90 (s, 3H),

| Example No. | Structure | Reactant; yield [% of theory] | $^1$H NMR (400 MHz, CDCl$_3$) LC/MS: $R_t$ [Method] |
|---|---|---|---|
| 18 | 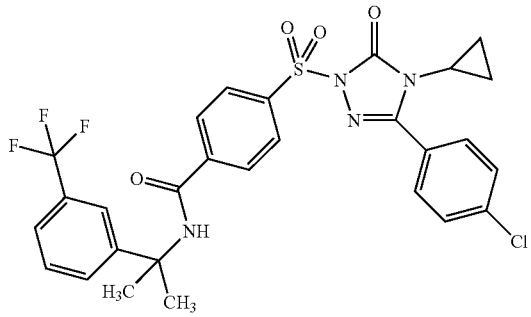 [SMILES: CC(C)(NC(=O)c1ccc(S(=O)(=O)n2nc(-c3ccc(Cl)cc3)n(C3CC3)c2=O)cc1)c1cccc(C(F)(F)F)c1] | 15A; 18% | δ = 0.67-0.76 (m, 2 H), 0.94-1.03 (m, 2 H), 1.82 (s, 6 H), 2.81-2.89 (m, 1 H), 6.48 (br. s., 1 H), 7.43-7.59 (m, 4 H), 7.43-7.73 (m, 4 H), 7.92 (d, 2 H), 8.23 (d, 2 H). LC-MS [2]: $R_t$ = 2.50 min; MS [ESIpos]: m/z = 605 (M + H)$^+$ |
| 19 | 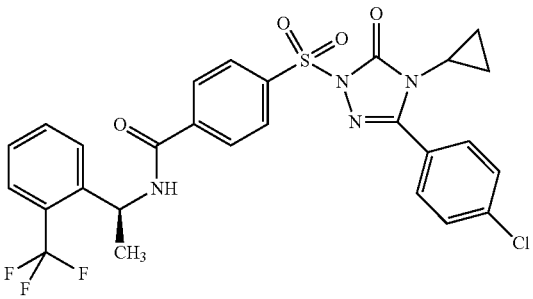 [SMILES: C[C@H](NC(=O)c1ccc(S(=O)(=O)n2nc(-c3ccc(Cl)cc3)n(C3CC3)c2=O)cc1)c1ccccc1C(F)(F)F] | 15A; 20% | δ = 0.66-0.74 (m, 2 H), 0.94-1.02 (m, 2 H), 1.61 (d, 3 H), 2.80-2.89 (m, 1 H), 5.59 (qt, 1 H), 6.52 (d, 1 H), 7.36-7.43 (m, 1 H), 7.46 (d, 2 H), 7.57 (d, 2 H), 7.62-7.75 (m, 3 H), 7.93 (d, 2 H), 8.19 (d, 2 H). LC-MS [3]: $R_t$ = 2.75 min; MS [ESIpos]: m/z 591 (M + H)$^+$ |

5.06 (s, 2H), 5.91 (br. s, 1H), 7.09 (dd, 1H), 7.16 (d, 2H), 7.38 (d, 1H), 7.43 (d, 2H), 7.67 (d, 2H).

Example 21

4-{[3-(4-Chlorophenyl)-4-cyclopropyl-5-oxo-4,5-dihydro-1H-1,2,4-triazol-1-yl]methyl}-3-methoxy-N-{2-[3-(trifluoromethyl)phenyl]propan-2-yl}benzamide

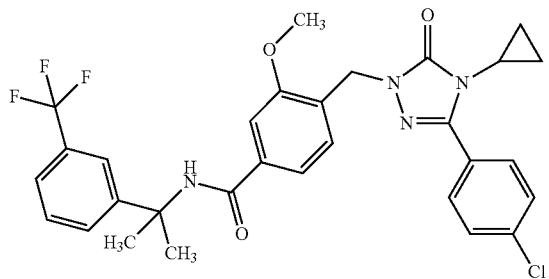 [SMILES: COc1cc(C(=O)NC(C)(C)c2cccc(C(F)(F)F)c2)ccc1Cn1nc(-c2ccc(Cl)cc2)n(C2CC2)c1=O]

In the same way as for the compound from Example 20, 61 mg (83% of theory) of the target compound were obtained from 50 mg (0.13 mmol) of the compound from Example 21A.

LC/MS [Method 2] $R_t$=2.40 min; MS [ESIpos]: m/z=585 (M+H)$^+$ $^1$H NMR (400 MHz, CDCl$_3$): δ=0.75-0.80 (m, 2H), 1.00-1.07 (m, 2H), 1.80 (s, 6H), 3.00 (spt, 1H), 3.88 (s, 3H), 5.07 (s, 2H), 6.43 (s, 1H), 7.17-7.23 (m, 2H), 7.37 (s, 1H), 7.41-7.51 (m, 4H), 7.61 (d, 1H), 7.63-7.69 (m, 3H).

Example 22

N-tert-Butyl-4-{[3-(4-chlorophenyl)-4-cyclopropyl-5-oxo-4,5-dihydro-1H-1,2,4-triazol-1-yl]methyl}-2-methoxybenzamide

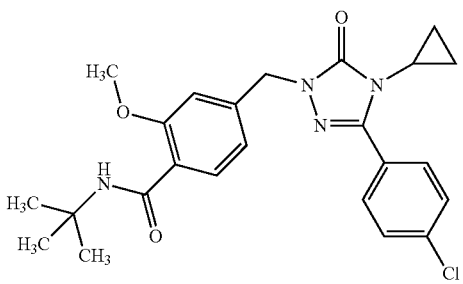 [SMILES: COc1cc(Cn2nc(-c3ccc(Cl)cc3)n(C3CC3)c2=O)ccc1C(=O)NC(C)(C)C]

An amount of 70 mg (0.30 mmol) of 5-(4-chlorophenyl)-4-cyclopropyl-2,4-dihydro-3H-1,2,4-triazol-3-one (preparation as per WO 2007/134862 Example 36A) was dissolved in 3 ml of DMF and admixed with 194 mg (0.59 mmol) of caesium carbonate and also 98 mg (0.33 mmol) of the compound from Example 23A. The mixture was stirred at 70° C. for 16 h. After cooling to RT, the crude mixture was freed from insoluble constituents by filtration and subjected directly to chromatographic purification [Method 8]. This gave 89 mg (66% of theory) of the target compound.

LC/MS [Method 2] $R_t$=2.12 min; MS [ESIpos]: m/z=455 (M+H)$^+$ $^1$H NMR (400 MHz, CDCl$_3$): δ=0.72-0.78 (m, 2H), 0.99-1.05 (m, 2H), 1.44 (s, 9H), 2.94-3.01 (m, 1H), 3.95 (s, 3H), 4.98 (s, 2H), 7.03 (s, 1H), 7.09 (d, 1H), 7.44 (d, 2H), 7.65 (d, 2H), 7.76 (br. s., 1H), 8.13 (d, 1H).

Example 23

N-tert-Butyl-4-{[3-(4-chlorophenyl)-5-oxo-4-(3,3,3-trifluoro-2-hydroxypropyl)-4,5-dihydro-1H-1,2,4-triazol-1-yl]methyl}benzamide

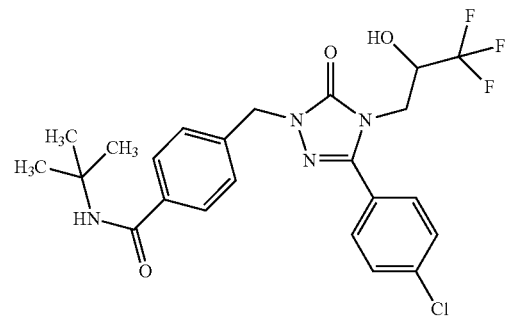 [SMILES: CC(C)(C)NC(=O)c1ccc(Cn2nc(-c3ccc(Cl)cc3)n(CC(O)C(F)(F)F)c2=O)cc1]

An amount of 50 mg (0.11 mmol) of the compound from Example 28A was introduced in 1 ml of DMF and admixed with 18 mg (0.14 mmol) of HOBt and with 28 mg (0.15 mmol) of EDC. After 10 minutes of stirring at RT, 13 μl (0.12 mmol) of 2-methylpropan-2-amine were added and the mixture was stirred at room temperature for 16 h. Subsequently the reaction solution was admixed with about 3 ml of water and extracted with twice 5 ml of ethyl acetate. The combined organic phases were dried over sodium sulphate, filtered and concentrated under reduced pressure. The crude product was purified by chromatography [Method 8]. This gave 31 mg (55% of theory) of the target compound.

LC/MS [Method 4] $R_t$=1.29 min; MS [ESIpos]: m/z=497 (M+H)$^+$ $^1$H NMR (400 MHz, CDCl$_3$): δ=1.46 (s, 9H), 3.95-4.09 (m, 2H), 4.40-4.50 (m, 1H), 4.98-5.14 (m, 3H), 5.93 (s, 1H), 7.40 (d, 2H), 7.44-7.53 (m, 4H), 7.65 (d, 2H).

Example 24

4-{[3-(4-Chlorophenyl)-5-oxo-4-(3,3,3-trifluoro-2-hydroxypropyl)-4,5-dihydro-1H-1,2,4-triazol-1-yl]methyl}-N-{2-[3-(trifluoromethyl)phenyl]propan-2-yl}benzamide

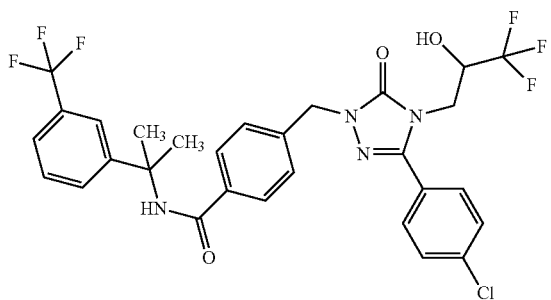 [SMILES: CC(C)(NC(=O)c1ccc(Cn2nc(-c3ccc(Cl)cc3)n(CC(O)C(F)(F)F)c2=O)cc1)c1cccc(C(F)(F)F)c1]

In the same way as for the compound from Example 23, 28 mg (40% of theory) of the target compound were obtained from 50 mg (0.11 mmol) of the compound from Example 28A.

LC/MS [Method 4] $R_t$=1.46 min; MS [ESIpos]: m/z=627 (M+H)$^+$ $^1$H NMR (400 MHz, CDCl$_3$): δ=1.80 (s, 6H), 3.94-4.08 (m, 2H), 4.37-4.49 (m, 1H), 4.99-5.13 (m, 3H), 6.45 (s, 1H), 7.38-7.54 (m, 8H), 7.60 (d, 1H), 7.64 (s, 1H), 7.69 (d, 2H).

Example 25

N-tert-Butyl-3-{[3-(4-chlorophenyl)-5-oxo-4-(3,3,3-trifluoro-3-hydroxypropyl)-4,5-dihydro-1H-1,2,4-triazol-1-yl]methyl}benzamide

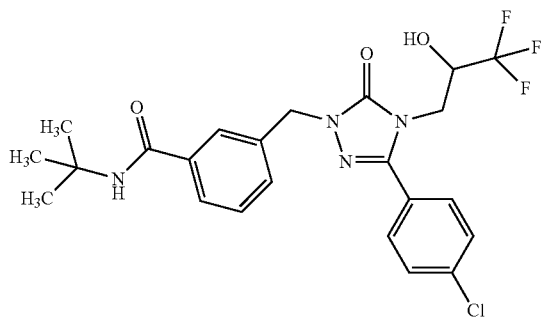 [SMILES: CC(C)(C)NC(=O)c1cccc(Cn2nc(-c3ccc(Cl)cc3)n(CC(O)C(F)(F)F)c2=O)c1]

In the same way as for the compound from Example 23, 49 mg (87% of theory) of the target compound were obtained from 50 mg (0.11 mmol) of the compound from Example 29A.

LC/MS [Method 4] $R_t$=1.30 min; MS [ESIpos]: m/z=497 (M+H)$^+$ $^1$H NMR (400 MHz, CDCl$_3$): δ=1.44 (s, 9H), 3.96 (dd, 1H), 4.06-4.14 (m, 1H), 4.54-4.65 (m, 1H), 5.00 and 5.24 (2d, 2H), 5.98 (d, 1H), 6.01 (s, 1H), 7.33-7.53 (m, 6H), 7.59 (d, 2H).

Example 26

3-{[3-(4-Chlorophenyl)-5-oxo-4-(3,3,3-trifluoro-2-hydroxypropyl)-4,5-dihydro-1H-1,2,4-triazol-1-yl]methyl}-N-{2,2-difluoro-2-[2-(trifluoromethyl)phenyl]ethyl}benzamide

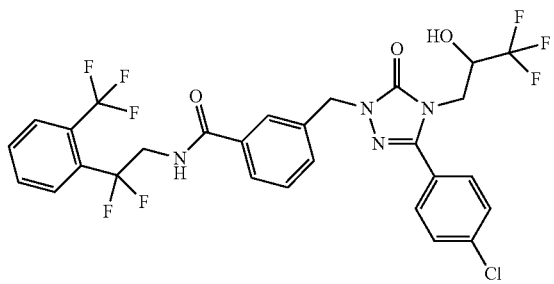 [SMILES: O=C(NCC(F)(F)c1ccccc1C(F)(F)F)c1cccc(Cn2nc(-c3ccc(Cl)cc3)n(CC(O)C(F)(F)F)c2=O)c1]

In the same way as for the compound from Example 23, 40 mg (68% of theory) of the target compound were obtained from 41 mg (0.09 mmol) of the compound from Example 29A.

LC/MS [Method 4] $R_t$=1.41 min; MS [ESIpos]: m/z=649 (M+H)$^+$ $^1$H NMR (400 MHz, CDCl$_3$): δ=3.97 (dd, 1H), 4.04-4.25 (m, 3H), 4.46-4.60 (m, 1H), 5.02 and 5.19 (2d, 2H), 5.41 (d, 1H), 6.62 (t, 1H), 7.39-7.49 (m, 3H), 7.50-7.71 (m, 8H), 7.82 (d, 1H).

Example 27

N-tert-Butyl-3-chloro-4-{[3-(4-chlorophenyl)-4-cyclopropyl-5-oxo-4,5-dihydro-1H-1,2,4-triazol-1-yl]methyl}benzamide

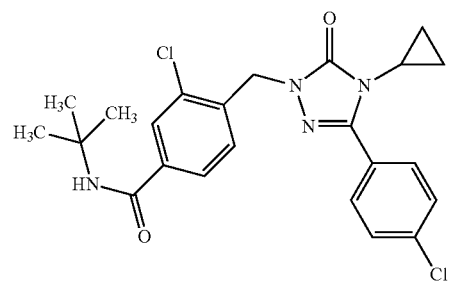 [SMILES: CC(C)(C)NC(=O)c1ccc(Cn2nc(-c3ccc(Cl)cc3)n(C3CC3)c2=O)c(Cl)c1]

In the same way as for the compound from Example 23, 9 mg (15% of theory) of the target compound were obtained from 88 mg (about 0.13 mmol) of the compound from Example 27A.

LC/MS [Method 4] $R_t$=1.35 min; MS [ESIpos]: m/z=459 and 461 (M+H)$^+$ $^1$H NMR (400 MHz, CDCl$_3$): δ=0.75-0.82 (m, 2H), 1.00-1.08 (m, 2H), 1.45 (s, 9H), 3.01 (spt, 1H), 5.15 (s, 2H), 5.85 (br. s., 1H), 7.29 (d, 1H), 7.44 (d, 2H), 7.56 (dd, 1H), 7.67 (d, 2H), 7.73 (d, 1H).

B. EVALUATION OF THE PHARMACOLOGICAL ACTIVITY

Abbreviations

EDTA Ethylenediaminetetraacetic acid
DMEM Dulbecco's Modified Eagle Medium
FCS Foetal calf serum
HEPES 4-(2-Hydroxyethyl)-1-piperazineethanesulphonic acid
SmGM Smooth Muscle Cell Growth Media
Tris-HCl 2-Amino-2-(hydroxymethyl)-1,3-propanediol hydrochloride
UtSMC Uterine Smooth Muscle Cells B-1. Cellular In Vitro Assay for Determining the Vasopressin Receptor Activity The identification of agonists and antagonists of the V1a and V2 vasopressin receptors from humans and rats and also the quantification of the activity of the substances described here took place using recombinant cell lines. These cells derive originally from a hamster ovary epithelial cell (Chinese Hamster Ovary, CHO K1, ATCC: American Type Culture Collection, Manassas, Va. 20108, USA). The test cell lines constitutively express a modified form of the calcium-sensitive photoprotein aequorin, which, after reconstitution with the cofactor coelenterazine, emits light when there are increases in the free calcium concentration (Rizzuto R., Simpson A. W., Brini M., Pozzan T.; Nature 358 (1992) 325-327). In addition, the cells are stably transfected with the human or rat V1a or V2 receptors. In the case of the Gs-coupling V2 receptors, the cells are stably transfected with a further gene, which codes for the promiscuous $G_{\alpha16}$ protein (Amatruda T. T., Steele D. A., Slepak V. Z., Simon M. I., *Proc. Nat. Acad. Sci. USA* 88 (1991), 5587-5591), either independently or as a fusion gene. The resulting vasopressin receptor test cells react to stimulation of the recombinantly expressed vasopressin receptors by intracellular release of calcium ions, which can be quantified by the resulting aequorin luminescence using a suitable luminometer (Milligan G., Marshall F., Rees S., *Trends in Pharmaco. Sci.* 17 (1996) 235-237).

Test Procedure:

On the day before the assay, the cells are plated out in culture medium (DMEM, 10% FCS, 2 mM glutamine, 10 mM HEPES) in 384-well microtiter plates and kept in a cell incubator (96% humidity, 5% v/v carbon dioxide, 37° C.). On the day of the assay, the culture medium is replaced by a Tyrode solution (140 mM sodium chloride, 5 mM potassium chloride, 1 mM magnesium chloride, 2 mM calcium chloride, 20 mM glucose, 20 mM HEPES), which additionally contains the cofactor coelenterazine (50 μM), and the microtiter plate is then incubated for a further 3-4 hours. The test substances in various concentrations are placed for 10 to 20 minutes in the wells of the microtiter plate before the agonist [Arg8]-vasopressin is added, and the resulting light signal is measured immediately in the luminometer. The IC50 values are calculated using the GraphPad PRISM computer program (Version 3.02).

The table below lists representative $IC_{50}$ values for the compounds of the invention on the cell line transfected with the human V1a or V2 receptor:

TABLE 1

| Example No. | $IC_{50}$ hV1a [μM] | $IC_{50}$ hV2 [μM] |
|---|---|---|
| 1 | 5.5 | 0.003 |
| 2 | 3.7 | 0.003 |
| 3 | >25 | 0.013 |
| 7 | >25 | 0.007 |
| 13 | 3.5 | 0.29 |
| 14 | >25 | 0.009 |
| 17 | 7.1 | 0.004 |
| 20 | 15.2 | 0.004 |
| 22 | 0.87 | 0.22 |
| 27 | 4.2 | 0.027 |

B-2. Cellular In Vitro Assay for Detecting the Action of Vasopressin V1a Receptor Antagonists on the Regulation of Pro-Fibrotic Genes The cell line H9C2 described as of cardiomyocyte type (American Type Culture Collection ATCC No. CRL-1446), isolated from rat cardiac tissue, endogenously expresses the vasopressin V1A receptor AVPR1A in high copy number, whereas the AVPR2 expression cannot be detected. For cell assays on the inhibition of the AVPR1A receptor-dependent regulation of gene expression by receptor antagonists, the procedure is as follows:

H9C2 cells are seeded in 12-well microtiter plates for cell culture, at a cell density of 100 000 cells/well, in 1.0 ml of Opti-MEM medium (Invitrogen Corp. Carlsbad Calif., USA, Cat. No. 11058-021) with 2% FCS and 1% penicillin/streptomycin solution (Invitrogen Cat. No. 10378-016), and held in a cell incubator (96% humidity, 5% v/v carbon dioxide, 37° C.). After 24 hours, sets of three wells (triplicate) are charged with vehicle solution (negative control), vasopressin solution: [Arg8]-vasopressin acetate (Sigma Cat. No. V9879) or test substances (dissolved in vehicle: water with 20% by volume ethanol) and vasopressin solution. In the cell culture, the final vasopressin concentration is 0.05 μM. The test substance solution is added to the cell culture in small volumes, and so a final concentration of 0.1% of ethanol in the cell assay is not exceeded. After an incubation time of 6 hours, the culture supernatant is drawn off under suction, the adherent cells are lysed in 250 μl of RLT buffer (Qiagen, Ratingen, Cat. No. 79216), and the RNA is isolated from this lysate using the RNeasy kit (Qiagen, Cat. No. 74104). This is followed by DNAse digestion (Invitrogen Cat. No. 18068-015), cDNA synthesis (Promaga ImProm-II Reverse Transcription System Cat. No. A3800) and RTPCR using the pPCR MasterMix RT-QP2X-03-075 from Eurogentec, Seraing, Belgium. All procedures take place in accordance with the working protocols of the test reagents' manufacturers. The primer sets for the RTPCR are selected on the basis of the mRNA gene sequences (NCBI Genbank Entrez Nucleotide Data Base) using the Primer3Plus program with 6-FAM-TAMRA labelled probes. The RTPCR for determining the relative mRNA expression in the cells of the various assay batches is carried out using the Applied Biosystems ABI Prism 7700 Sequence Detector in 96-well or 384-well microtiter plate format in accordance with the instrument operating instructions. The relative gene expression is represented by the delta-delta Ct value [Applied Biosystems, User Bulletin No. 2 ABI Prism 7700 SDS Dec. 11, 1997 (updated 10/2001)] with reference to the level of expression of the ribosomal protein L-32 gene (Genbank Acc. No. NM_013226) and the threshold Ct value of Ct=35.

B-3. In Vivo Test for Detection of Cardiovascular Effect: Blood Pressure Measurement on Anaesthetised Rats (Vasopressin 'Challenge' Model)

In male Sprague-Dawley rats (250-350 g body weight) under ketamine/xylazine/pentobarbital injection anaesthesia, polyethylene tubes (PE-50; Intramedic®), which are prefilled with heparin-containing (500 IU/ml) isotonic sodium chloride solution, are introduced into the jugular vein and the femoral vein and then tied in. Via one venous access, with the aid of a syringe, arginine-vasopressin is injected; the test substances are administered via the second venous access. For determination of the cystolic blood pressure, a pressure catheter (Millar SPR-320 2F) is tied into the carotid artery. The arterial catheter is connected to a pressure transducer which feeds its signals to a recording computer equipped with suitable recording software. In a typical experiment the experimental animal is administered 3-4 successive bolus injections at intervals of 10-15 min with a defined amount of arginine-vasopressin (30 ng/kg) in isotonic sodium chloride solution and, when the blood pressure has reached initial levels again, the substance under test is administered as a bolus, with subsequent ongoing infusion, in a suitable solvent. After this, at defined intervals (10-15 min), the same amount of vasopressin as at the start is administered again. On the basis of the blood pressure values, a determination is made of the extent to which the test substance counteracts the hypertensive effect of the vasopressin. Control animals receive only solvent instead of the test substance.

Following intravenous administration, the compounds of the invention, in comparison to the solvent controls, bring about an inhibition in the blood pressure increase caused by arginine-vasopressin.

B-4. In Vivo Assay for Detecting the Cardiovascular Effect: Diuresis Investigations on Conscious Rats in Metabolism Cages Wistar rats (220-400 g body weight) are kept with free access to feed (Altromin) and drinking water. During the experiment, the animals are kept with free access to drinking water for 4 to 8 hours individually in metabolism cages suitable for rats of this weight class (Tecniplast Deutschland GmbH, D-82383 Hohenpeißenberg). At the beginning of the experiment, the animals are administered the substance under test in a volume of 1 to 3 ml/kg body weight of a suitable solvent by means of gavage into the stomach. Control animals receive only solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per unit time is determined separately for each animal, and the concentration of the sodium and potassium ions excreted in the urine is measured by standard methods of flame photometry. To obtain a sufficient volume of urine, the animals are given a defined amount of water by gavage at the beginning of the experiment (typically 10 ml per kilogram of body weight). Before the beginning of the experiment and after the end of the experiment, the body weight of the individual animals is taken.

Following oral administration, in comparison with control animals, the compounds of the invention bring about an increased excretion of urine, which is based essentially on an increased excretion of water (aquaresis).

B-5. In Vivo Assay for Detecting the Cardiovascular Effect: Haemodynamic Investigations on Anaesthetised Dogs Male or female mongrel dogs (Mongrels, Marshall BioResources, USA) with a weight of between 20 and 30 kg are anaesthetised with pentobarbital (30 mg/kg iv, Narcoren®, Merial, Germany) for the surgical interventions and the haemodynamic and functional investigation terminii. Alcuronium chloride (Alloferin®, ICN Pharmaceuticals, Germany, 3 mg/animal iv) serves additionally as a muscle relaxant. The dogs are intubated and ventilated with an oxygen/ambient air mixture (40/60%) (about 5-6 L/min). Ventilation takes place using a ventilator from Draeger (Sulla 808) and is monitored using a carbon dioxide analyser (Engström).

The anaesthesia is maintained by continual infusion of pentobarbital (50 µg/kg/min); fentanyl is used as an analgesic (10 µg/kg/h). One alternative to pentobarbital is to use isoflurane (1-2% by volume).

In preparatory interventions, the dogs are fitted with a cardiac pacemaker.

At a time of 21 days before the first drug testing (i.e. start of experiment), a cardiac pacemaker from Biotronik (Logos®) is implanted into a subcutaneous skin pocket and is contacted with the heart via a pacemaker electrode which is advanced through the external jugular vein, with illumination, into the right ventricle.

At the same time as the implanting of the pacemaker, through retrograde advancing of a 7F biopsy forceps (Cordis) via a sheath introducer (Avanti+®; Cordis) in the femoral artery, and after atraumatic passage through the aortic valve, there is defined lesion of the mitral valve, with monitoring by echo cardiography and illumination. Thereafter all of the accesses are removed and the dog wakes spontaneously from the anaesthesia.

After a further 7 days (i.e. 14 days before the first drug testing), the above pacemaker is activated and the heart is stimulated at a frequency of 220 beats per minute.

The actual drug testing experiments take place 14 and 28 days after the beginning of pacemaker stimulation, using the following instrumentation:

Bladder catheter for bladder relief and for measuring the flow of urine

ECG leads to the extremities (for ECG measurement)

Introduction of an NaCl-filled Fluidmedic PE-300 tube into the femoral artery. This tube is connected to a pressure sensor (Braun Melsungen, Melsungen, Germany) for measuring the systemic blood pressure Introduction of a Millar Tip catheter (type 350 PC, Millar Instruments, Houston, USA) through the left atrium or through a port secured in the carotid artery, for measuring cardiac haemodynamics Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure Siting of a Braunüle in the cephalic vein, for infusing pentobarbital, for liquid replacement and for blood sampling (determination of the plasma levels of substance or other clinical blood values)

Siting of a Braunüle in the saphenous vein, for infusing fentanyl and for administration of substance Infusion of vasopressin (Sigma) in increasing dosage, up to a dose of 4 mU/kg/min. The pharmacological substances are then tested with this dosage.

The primary signals are amplified if necessary (Gould amplifier, Gould Instrument Systems, Valley View, USA) or Edwards Vigilance-Monitor (Edwards, Irvine, USA) and subsequently fed into the Ponemah system (DataSciences Inc, Minneapolis, USA) for evaluation. The signals are recorded continuously throughout the experimental period, and are further processed digitally by the said software, and averaged over 30 s.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% strength solution (m/m) of the PVP in water. After drying, the granules are mixed with the magnesium stearate for 5 minutes. This mixture is compressed using a conventional tableting press (for tablet format see above). The guideline compressive force used for compression is 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

A single dose of 100 mg of the compound of the invention is given by 10 ml of oral suspension.

Production:

The Rhodigel is suspended in ethanol, and the compound of the invention is added to the suspension. The water is added with stirring. Stirring is continued for about 6 h until the swelling of the Rhodigel is ended.

Solution for Oral Administration:

Composition:

500 mg of the compound of the invention, 2.5 g of polysorbate and 97 g of polyethylene glycol 400. A single dose of 100 mg of the compound of the invention is given by 20 g of oral solution.

Production:

The compound of the invention is suspended with stirring in the mixture of polyethylene glycol and polysorbate. The stirring operation continues until the compound of the invention is fully dissolved.

I.V. Solution:

The compound of the invention is dissolved at a concentration below saturation solubility in a physiologically tolerated solvent (e.g. isotonic saline solution, 5% glucose solution and/or 30% PEG 400 solution). The solution is sterile-filtered and dispensed into sterile, pyrogen-free injection containers.

The invention claimed is:

1. Compound of the formula (I)

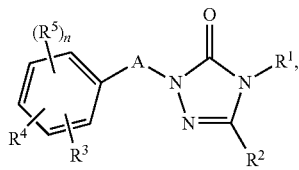

(I)

in which

A is —CH$_2$— or —SO$_2$—,

R$^1$ is hydrogen, (C$_1$-C$_6$) alkyl, (C$_2$-C$_6$) alkenyl, (C$_2$-C$_6$) alkynyl or (C$_3$-C$_7$) cycloalkyl, where (C$_1$-C$_6$) alkyl, (C$_2$-C$_6$) alkenyl and (C$_2$-C$_6$) alkynyl may be substituted by 1 to 3 substituents independently of one another selected from the group consisting of halogen, cyano, oxo, trifluoromethyl, (C$_3$-C$_7$) cycloalkyl, phenyl, —OR$^{10}$, —NR$^{11}$R$^{12}$, —C(=O)—OR$^{13}$ and —C(=O)—NR$^{14}$R$^{15}$, in which (C$_3$-C$_7$) cycloalkyl may be substituted by 1 or 2 substituents independently of one another selected from the group consisting of (C$_1$-C$_4$) alkyl, oxo, hydroxyl, (C$_1$-C$_4$) alkoxy and amino, and in which phenyl may be substituted by 1 to 3 substituents independently of one another selected from the group consisting of halogen, cyano, nitro, (C$_1$-C$_4$) alkyl, trifluoromethyl, hydroxyl, hydroxymethyl, (C$_1$-C$_4$) alkoxy, trifluoromethoxy, (C$_1$-C$_4$) alkoxymethyl, hydroxycarbonyl, (C$_1$-C$_4$) alkoxycarbonyl, aminocarbonyl, mono-(C$_1$-C$_4$) alkylaminocarbonyl and di-(C$_1$-C$_4$) alkylaminocarbonyl, and in which R$^{10}$, R$^{11}$, R$^{12}$, R$^{13}$, R$^{14}$ and R$^{15}$ are each independently of one another hydrogen or (C$_1$-C$_6$) alkyl, in which (C$_1$-C$_6$) alkyl may on its part be substituted by 1 or 2 substituents independently of one another selected from the group consisting of amino, hydroxyl, (C$_1$-C$_4$) alkoxy, hydroxycarbonyl and (C$_1$-C$_4$) alkoxycarbonyl, and where (C$_3$-C$_7$) cycloalkyl may be substituted by 1 or 2 substituents independently of one another selected from the group consisting of (C$_1$-C$_4$) alkyl, (C$_1$-C$_4$) alkoxy, hydroxy, amino and oxo, R$^2$ is halogen, trifluoromethyl, (C$_1$-C$_6$) alkyl, (C$_1$-C$_6$) alkoxy, mono-(C$_1$-C$_6$)-alkylamino, di-(C$_1$-C$_6$)-alkylamino, (C$_3$-C$_7$) cycloalkyl, phenyl, thienyl or furyl, where phenyl, thienyl and furyl may be substituted by 1 to 3 substituents independently of one another selected from the group consisting of halogen, cyano, nitro, (C$_1$-C$_4$) alkyl, trifluoromethyl, hydroxyl, (C$_1$-C$_4$) alkoxy and trifluoromethoxy, R$^3$ is hydrogen or (C$_1$-C$_4$) alkoxy, R$^4$ is (C$_1$-C$_6$) alkylcarbonyl, mono-(C$_1$-C$_6$)-alkylaminocarbonyl or di-(C$_1$-C$_6$) alkylaminocarbonyl, where (C$_1$-C$_6$)-alkylcarbonyl, mono-(C$_1$-C$_6$)-alkylaminocarbonyl and di-(C$_1$-C$_6$)-alkylaminocarbonyl may be substituted by 1 to 4 substituents independently of one another selected from the group consisting of halogen, trifluoromethyl, (C$_1$-C$_6$) alkyl and phenyl, in which phenyl may be substituted by 1 or 2 substituents independently of one another selected from the group consisting of halogen, cyano, trifluoromethyl, hydroxyl-(C$_1$-C$_4$) alkyl, (C$_1$-C$_4$) alkyl, trifluoromethoxy and (C$_1$-C$_4$) alkoxy, R$^5$ is halogen, trifluoromethyl, (C$_1$-C$_4$) alkyl, trifluoromethoxy or (C$_1$-C$_4$) alkoxy, n is a number 0, 1 or 2, and salts thereof.

2. The compound of claim 1, in which

A is —CH$_2$— or —SO$_2$—,

R$^1$ is hydrogen, (C$_1$-C$_6$) alkyl, (C$_2$-C$_4$) alkenyl or (C$_3$-C$_6$) cycloalkyl, where (C$_1$-C$_6$) alkyl and (C$_2$-C$_4$) alkenyl may be substituted by 1 to 3 substituents independently of one another selected from the group consisting of fluorine, chlorine, oxo, trifluoromethyl, (C$_3$-C$_6$) cycloalkyl, phenyl, —OR$^{10}$, —NR$^{11}$R$^{12}$, —C(=O)—OR$^{13}$ and —C(=O)—NR$^{14}$R$^{15}$, in which phenyl may be substituted by 1 to 3 substituents independently of one another selected from the group consisting of fluorine, chlorine, (C$_1$-C$_4$) alkyl, trifluoromethyl, hydroxyl, (C$_1$-C$_4$) alkoxy, trifluoromethoxy, hydroxycarbonyl, (C$_1$-C$_4$) alkoxycarbonyl, aminocarbonyl, mono-(C$_1$-C$_4$)-alkylaminocarbonyl and di-(C$_1$-C$_4$)-alkylaminocarbonyl, and in which R$^{10}$, R$^{11}$, R$^{12}$, R$^{13}$, R$^{14}$ and R$^{15}$ independently of one another are each hydrogen or (C$_1$-C$_6$) alkyl, R$^2$ is chlorine, bromine, trifluoromethyl, (C$_1$-C$_4$) alkyl, (C$_1$-C$_4$) alkoxy, mono-(C$_1$-C$_4$)-alkylamino, di-(C$_1$-C$_4$)-alkylamino, (C$_3$-C$_6$) cycloalkyl or phenyl, where phenyl may be substituted by 1 to 3 substituents independently of one another selected from the group consisting of fluorine, chlorine, cyano, methyl, ethyl, trifluoromethyl, hydroxyl, methoxy, ethoxy and trifluoromethoxy, R$^3$ is hydrogen or methoxy, R$^4$ is (C$_1$-C$_6$) alkylcarbonyl, mono-(C$_1$-C$_6$)-alkylaminocarbonyl or di-(C$_1$-C$_6$)-alkylaminocarbonyl, where mono-(C$_1$-C$_6$)-alkylaminocarbonyl and di-(C$_1$-C$_6$)-alkylaminocarbonyl may be substituted by 1 to 4 substituents independently of one another selected from the group consisting of fluorine, trifluoromethyl, (C$_1$-C$_4$) alkyl and phenyl, in which phenyl may be substituted by 1 or 2 substituents independently of one another selected from the group consisting of fluorine, chlorine, trifluormethyl, methyl, ethyl, trifluoromethoxy, methoxy and ethoxy, $R^5$ is fluorine, chlorine, trifluoromethyl, methyl, ethyl, trifluoromethoxy, methoxy or ethoxy, n is a number 0 or 1, and salts thereof.

3. The compound of claim 1, in which

A is —CH$_2$— or —SO$_2$—, $R^1$ is hydrogen, (C$_1$-C$_6$) alkyl, (C$_2$-C$_4$) alkenyl or cyclopropyl, where (C$_1$-C$_6$) alkyl and (C$_2$-C$_4$) alkenyl may be substituted by 1 to 3 substituents independently of one another selected from the group consisting of fluorine, oxo, trifluoromethyl, phenyl, —OR$^{10}$, —NR$^{11}$R$^{12}$, —C(=O)—OR$^{13}$ and —C(=O)—NR$^{14}$R$^{15}$, in which phenyl may be substituted by 1 to 3 substituents independently of one another selected from the group consisting of fluorine, chlorine, methyl, ethyl, trifluoromethyl, hydroxyl, methoxy, ethoxy, trifluoromethoxy, hydroxycarbonyl, methoxycarbonyl and ethoxycarbonyl, and in which $R^{10}$, $R^{11}$, $R^{12}$, $R^{13}$, $R^{14}$ and $R^{15}$ independently of one another are each hydrogen or methyl, $R^2$ is chlorine, bromine, trifluoromethyl, (C$_1$-C$_4$) alkyl, (C$_1$-C$_4$) alkoxy, mono-(C$_1$-C$_4$)-alkylamino, di-(C$_1$-C$_4$)-alkylamino, cyclopropyl or phenyl, where phenyl may be substituted by 1 or 2 substituents independently of one another selected from the group consisting of fluorine, chlorine, methyl, ethyl, trifluoromethyl, hydroxyl, methoxy, ethoxy and trifluoromethoxy, $R^3$ is hydrogen or methoxy, $R^4$ is methylcarbonyl, ethylcarbonyl, mono-(C$_1$-C$_6$)-alkylaminocarbonyl or di-(C$_1$-C$_6$)-alkylaminocarbonyl, where mono-(C$_1$-C$_6$)-alkylaminocarbonyl and di-(C$_1$-C$_6$)-alkylaminocarbonyl may be substituted by 1 to 4 substituents independently of one another selected from the group consisting of fluorine, trifluoromethyl, methyl, ethyl and phenyl, in which phenyl may be substituted by 1 or 2 substituents independently of one another selected from the group consisting of fluorine, chlorine, trifluoromethyl, methyl, ethyl, trifluoromethoxy, methoxy and ethoxy, $R^5$ is fluorine, chlorine or trifluoromethyl, n is a number 0 or 1, and salts thereof.

4. A process for preparing a compound of claim 1, characterized in that:

[A] a compound of formula (II)

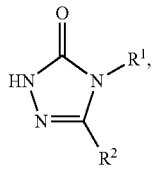

(II)

in which $R^1$ and $R^2$ are each as defined in claim 1 is reacted in an inert solvent, in the presence of a suitable base, with a compound of the formula (III)

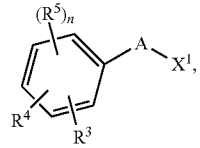

(III)

in which A, n, $R^3$, $R^4$ and $R^5$ are each as defined in claim 1, and $X^1$ is halogen, in particular chlorine, or

[B] from a compound of the formula (IV)

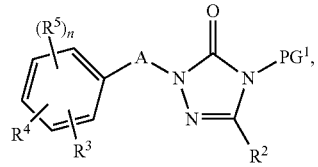

(IV)

in which A, n, $R^2$, $R^3$, $R^4$ and $R^5$ are each as defined in claim 1, and PG$^1$ is a suitable protective group, for example allyl, in an inert solvent by standard methods the protective group PG$^1$ is eliminated and the resulting compound of the formula (V)

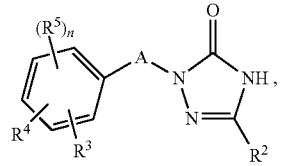

(V)

in which A, n, $R^2$, $R^3$, $R^4$ and $R^5$ are each as defined in claim 1, is reacted in the presence of a suitable base with a compound of the formula (VI)

$R^1$—$X^2$ (VI), in which $R^1$ is as defined in claim 1, and

X' is a leaving group, such as, for example, halogen, mesylate or tosylate, and the resulting compound of formula (I) are optionally converted with the corresponding base or acids into a salt thereof.

5. A pharmaceutical composition comprising a compound of the formula (I) as defined in claim 1 in combination with an inert, non-toxic, pharmaceutically suitable excipient.

6. The pharmaceutical composition of claim 5, further comprising at least one active ingredient selected from the group consisting of diuretics, angiotensin AII antagonists, ACE inhibitors, beta receptor blockers, mineralocorticoid receptor antagonists, organic nitrates, and NO donors.

7. A method of treatment of acute and chronic cardiac insufficiency, hypervolaemic and euvolaemic hyponatraemia, liver cirrhosis, ascites, oedemas and the syndrome of inadequate ADH secretion (SIADH) comprising administering to a patient in need thereof a compound of claim 1 or a pharmaceutical composition of claim 5.

* * * * *